United States Patent
Schwab et al.

(10) Patent No.: US 8,211,151 B2
(45) Date of Patent: Jul. 3, 2012

(54) DEVICES AND METHODS FOR DYNAMIC SPINAL STABILIZATION AND CORRECTION OF SPINAL DEFORMITIES

(75) Inventors: Frank J. Schwab, New York, NY (US); Carlos E. Gil, Collierville, TN (US); Jason Michael May, Cordova, TN (US); Aleksandr G. Zolotov, Collierville, TN (US)

(73) Assignee: Warsaw Orthopedic, Warsaw, IN (US)

( * ) Notice: Subject to any disclaimer, the term of this patent is extended or adjusted under 35 U.S.C. 154(b) by 357 days.

(21) Appl. No.: 12/609,880

(22) Filed: Oct. 30, 2009

(65) Prior Publication Data
US 2011/0106165 A1    May 5, 2011

(51) Int. Cl.
*A61B 17/70* (2006.01)
(52) U.S. Cl. .................................................... 606/264
(58) Field of Classification Search .......... 606/264–278, 606/280
See application file for complete search history.

(56) References Cited

U.S. PATENT DOCUMENTS

| | | | |
|---|---|---|---|
| 5,498,263 A * | 3/1996 | DiNello et al. | 606/292 |
| 5,575,819 A | 11/1996 | Amis | |
| 5,863,293 A | 1/1999 | Richelsoph | |
| 6,224,598 B1 * | 5/2001 | Jackson | 606/305 |
| 6,248,106 B1 | 6/2001 | Ferree | |
| 6,296,643 B1 | 10/2001 | Hopf et al. | |
| 6,299,613 B1 | 10/2001 | Ogilvie et al. | |
| 6,488,683 B2 | 12/2002 | Lieberman | |
| 6,524,311 B2 | 2/2003 | Gaines, Jr. | |
| 6,551,320 B2 | 4/2003 | Lieberman | |
| 6,616,669 B2 | 9/2003 | Ogilvie et al. | |
| 6,746,450 B1 | 6/2004 | Wall et al. | |
| 7,285,121 B2 | 10/2007 | Braun et al. | |
| 7,335,201 B2 * | 2/2008 | Doubler et al. | 606/264 |
| 7,563,281 B2 * | 7/2009 | Sears et al. | 623/17.11 |
| 7,722,648 B2 * | 5/2010 | Drewry et al. | 606/250 |
| 7,927,359 B2 * | 4/2011 | Trautwein et al. | 606/264 |
| 2004/0162558 A1 * | 8/2004 | Hegde et al. | 606/61 |
| 2005/0131412 A1 * | 6/2005 | Olevsky et al. | 606/69 |
| 2005/0216004 A1 | 9/2005 | Schwab | |
| 2006/0217715 A1 | 9/2006 | Serhan et al. | |

* cited by examiner

*Primary Examiner* — Eduardo C Robert
*Assistant Examiner* — James Palmer

(57) ABSTRACT

An apparatus for attachment to a vertebral body for correcting spinal deformities. The apparatus has a plate member having an upper surface and a lower surface. The upper surface having at least one receiving member defining a channel for receiving a flexible connection member. The at least one receiving member having a proximal portion and a distal portion. The proximal and distal portions interfacing along a frangible connection such that the at least one receiving member extends axially from the upper surface a first distance when the frangible connection is unbroken and the at least one receiving member extends axially from the upper surface a second distance when the frangible connection is broken. The second distance is less than the first distance.

18 Claims, 13 Drawing Sheets

US 8,211,151 B2

DEVICES AND METHODS FOR DYNAMIC SPINAL STABILIZATION AND CORRECTION OF SPINAL DEFORMITIES

BACKGROUND

There is a strong and growing need for devices and methods to correct spinal deformities, particularly for scoliosis. Current devices and methods include internal spinal fixation devices and even fusion of vertebrae along the spinal column to correct spinal deformities. Moreover, because of the profile of such devices, and the perceived lack of benefit to anterior access to the spine, the current methods involve posterior surgical approaches in order to avoid damage and trauma to the delicate internal anatomy located around the anterior portion of the spinal column. Additionally, internal spinal fixation devices use rigid, or non-flexible, spinal rods that are incapable of expansion and/or flexation. Therefore, a growing child who has scoliosis experiences either permanent loss of growth and mobility of portions of the spine, or multiple surgical procedures in order to gain some continued growth until definitive destruction of mobile joints through a fusion procedure.

Accordingly, devices, systems, and methods for correcting spinal deformities that overcome these shortcomings are needed.

SUMMARY

These and other aspects, forms, objects, features, and benefits of the present invention will become apparent from the following detailed drawings and description.

An apparatus for attachment to a vertebral body for correcting spinal deformities. The apparatus has a plate member having an upper surface and a lower surface. The upper surface having at least one receiving member defining a channel for receiving a flexible connection member. The at least one receiving member having a proximal portion and a distal portion. The proximal and distal portions interfacing along a frangible connection such that the at least one receiving member extends axially from the upper surface a first distance when the frangible connection is unbroken and the at least one receiving member extends axially from the upper surface a second distance when the frangible connection is broken. The second distance is less than the first distance.

A system for correcting spinal deformities. The system including a plate having an upper surface and a lower surface. The upper surface having at least one receiving member defining a channel and a groove radially extending along the upper surface at an angle from the channel. The channel extending through the receiving member and defining a first longitudinal axis. The receiving member having a first configuration in which the receiving member extends a first distance from the upper surface and a second configuration in which the receiving member extends a second distance from the upper surface, wherein the first distance is greater than the second distance. The system also has a flexible connection member extending through the channel of the plate and extending along the groove at the angle with respect to the channel. Additionally, the system has a locking member engaging the receiving member to rigidly secure the flexible connection member within the channel of the plate.

An apparatus for attachment to a vertebral body for correcting spinal deformities. The apparatus has a plate having an upper surface and a lower surface. The upper surface having a first end portion and an opposing second end portion. The first end portion having a receiving member defining a channel extending through the receiving member along a first longitudinal axis and defining a bore extending through the receiving member along a second longitudinal axis. The channel being configured for receiving a flexible connection member and the bore being configured to receive and guide a first fastener to secure the plate to the vertebral body. The second end portion having an aperture formed within the upper surface and extending through to the lower surface. The aperture being configured to receive and guide a second fastener to secure the plate to the vertebral body.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify the embodiments of this invention.

DETAILED DESCRIPTION

Figure 2:
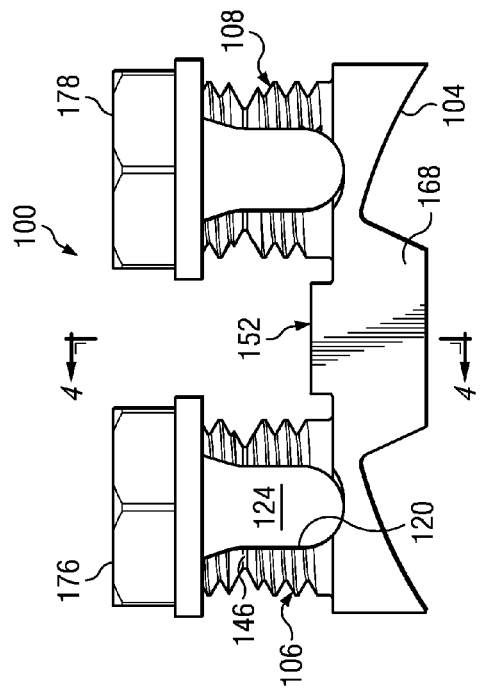
FIG. 2 is a side view of the plate of FIG. 1 with a pair of locking members positioned on a pair of posts of the plate.

The present disclosure relates generally to the field of orthopedic surgery, and more particularly to devices, systems and methods for correction of spinal deformities through the use of plate members allowing dynamic spinal stabilization. In addition, these devices, systems, and methods can be used for growth modulation and progressive three-dimensional correction or modification of deformity. For the purposes of promoting an understanding of the principles of the invention, reference will now be made to embodiments or examples illustrated in the drawings, and specific language will be used to describe these examples. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

Figure 3:
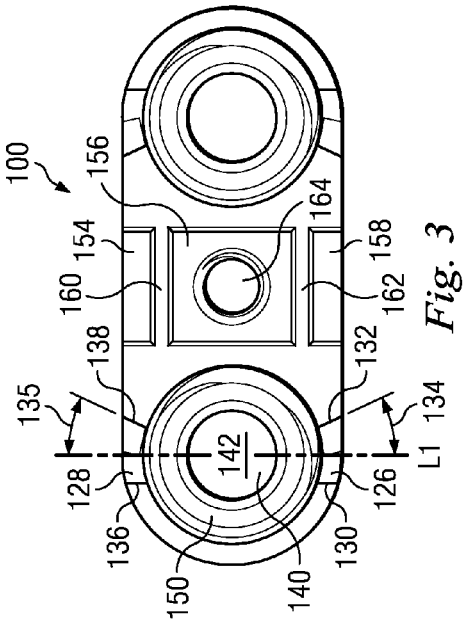
FIG. 3 is an overhead view of the plate of FIG. 1.
Figure 1:
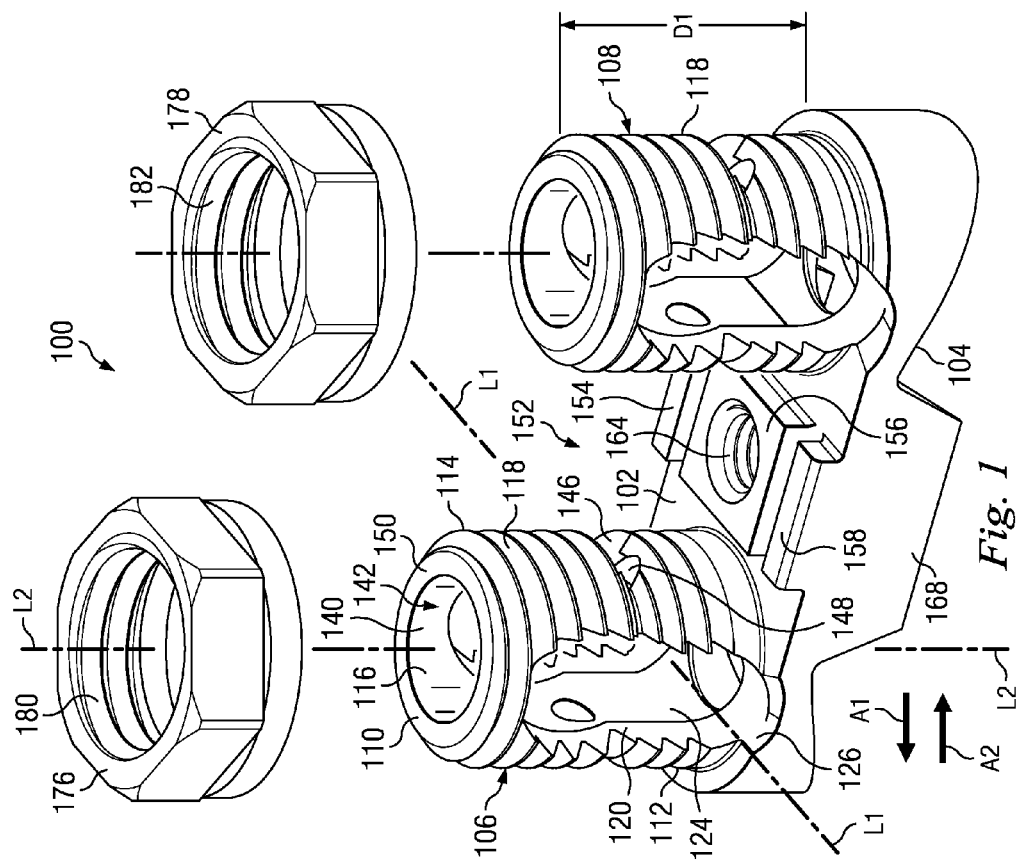
FIG. 1 is a perspective view of a plate for attachment to a bone structure according to one embodiment of the present disclosure.
Figure 4:
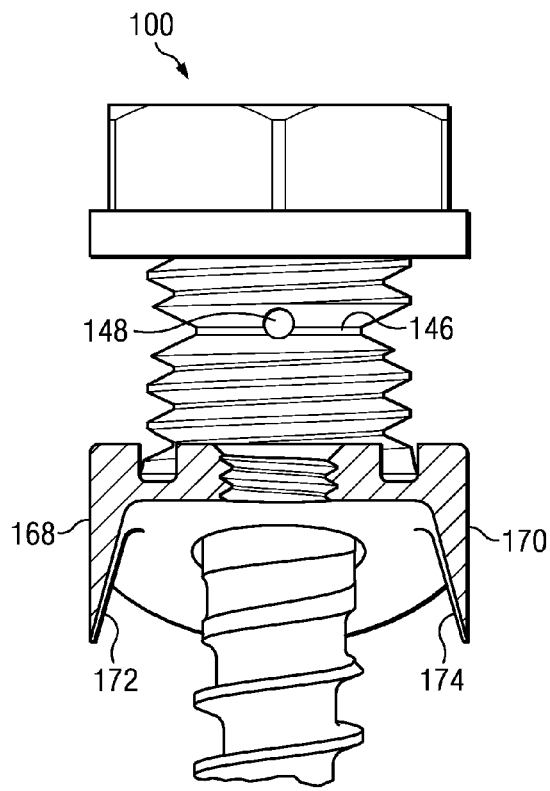
FIG. 4 is a cross-section view of an end section of the plate of FIG. 2.
Figure 5:
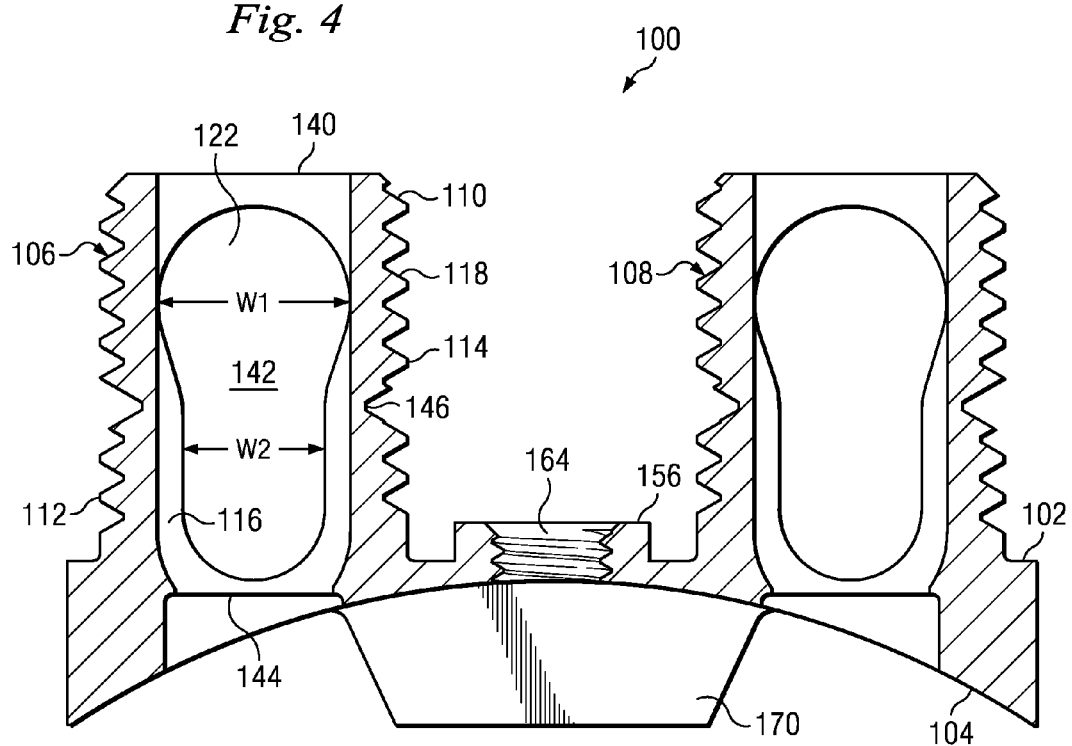
FIG. 5 is a cross-section view of the side view of the plate of FIG. 1.

FIGS. 1-5 show various views of an exemplary embodiment of a plate system for attachment to a bone structure. FIG. 1 is a perspective view of a plate for attachment to a bone structure according to one embodiment of the present disclosure. FIG. 2 is a side view of the plate of FIG. 1 with a pair of locking members positioned on a pair of posts of the plate. FIG. 3 is an overhead view of the plate of FIG. 1. FIG. 4 is a cross-section view of an end section of the plate of FIG. 2. FIG. 5 is a cross-section view of the side view of the plate of FIG. 1.

Referring first to FIG. 1, a perspective view of a plate member 100 for attachment to a bone structure, such as a vertebral body of a spinal column, is shown. Plate 100 is shown in an open or unlocked position ready to capture a flexible connection member such as a tether. Plate 100 has an upper surface 102 and a lower surface 104. A pair of posts 106 and 108, or receiving members, extend axially from the upper surface 102 at a distance D1. As an example, in one embodiment distance D1 can be about 14 millimeters. However, in other embodiments distance D1 can range from about 8 millimeters to about 20 millimeters. Moreover, in another embodiment distance D1 can range from about 1 millimeter to about 40 millimeters. Furthermore, it is contemplated that the distance D1 can be any distance in order to accommodate the passage of plate 100 within and around any anatomical structure of a patient's body.

Posts 106 and 108 have the same features. Therefore, the description of post 106 is applicable for post 108. Accordingly, like reference numerals are shown in the drawings to denote similar features for posts 106 and 108. However, features of post 108 will not be separately described herein.

Post 106 has a proximal portion 110 and a distal portion 112. An external surface 114 and an internal surface 116 of post 106 extend from the proximal portion 110 to the distal portion 112. Furthermore, internal surface 116 can extend below upper surface 102 thereby extending below distal portion 112. External surface 114 has external threads 118 that extend from the proximal portion 110 to the distal portion 112 of post 106. However, in other embodiments external threads 118 extend only partially from the proximal portion toward the distal portion of post 106.

With reference to FIGS. 1 and 5, external threads 118 are interrupted and truncated to form lateral openings 120 and 122 along the external surface 114 of post 106. Lateral openings 120 and 122 provide access to a channel 124, or a slot, extending through post 106 along an axis L1. It should be noted that the external surface 114 adjacent lateral opening can be rounded, smoothed, or chamfered in nature from the truncation of external threads 118. Thus, as described in more detail below, a flexible connection member passing though lateral openings 120 and 122 is not damaged by the external surface 114 adjacent the lateral openings.

As shown in FIG. 2 lateral openings 120 and 122 are in alignment with one another along axis L1. Furthermore, as shown in FIG. 5, lateral openings 120 and 122 are key-hole shape. In that regard, lateral openings 120 and 122 have an opening width W1 within the proximal portion 110 of post 106 that is wider than their respective opening width W2 within the distal portion 112 of post 106. Therefore, because the lateral openings 120 and 122 to channel 124 are key-hole shape then channel 124 can be considered as having a key-hole shape as well. As will be discussed in greater detail below, lateral openings 120 and 122 as well as channel 124 allow plate 100 to capture a flexible connection member such as a tether.

As best seen in FIGS. 2, 3, and 5, lateral openings 120 and 122 and thereby channel 124 extends below upper surface 102. Extending from the lateral openings 120 and 122 are grooves 126 and 128, or recesses, that are formed within upper surface 102. Groove 126 is bounded by end walls 130 and 132. End wall 130 extends substantially parallel with axis L1 and end wall 132 extends at an angle 134 with respect to axis L1. Angle 134 can range from about 0° to about 30° with respect to axis L1.

Similarly, groove 128 is bounded by end walls 136 and 138. End wall 136 extends substantially parallel with axis L1 and end wall 138 extends at an angle 135 with respect to axis L1. Angle 135 can range from about 0° to about 30° with respect to axis L1.

Therefore, grooves 126 and 128 allow a flexible connection member, or tether, received within channel 124 to extend through lateral openings 120 and 122 in parallel alignment with axis L1 and through angles ranging from about 0° to about 30° with respect to axis L1. It should be noted that angles 134 and 135 can be selected base on anatomical features and spinal deformities of a specific patient. In other words, depending on the type of spinal deformity, a plate having a specified angle for grooves 126 and/or 128 can be selected to correct the deformity.

With reference to FIGS. 1, 3, and 5, the proximal portion 110 of post 106 has a proximal opening 140 leading into a bore 142 extending along an axis L2. Internal surface 116 of post 106 defines bore 142 that extends through posts 106 and intersects channel 124. In that regard, bore 142 extend through post 142 substantially transverse to channel 124. However, in an alternative embodiment bore 142 and channel 124 can intersect one another at a non-transverse angle.

Bore 142 terminates at a distal opening 144. Internal surface 116 tapers near distal opening 144 to form a seat for accommodating a fastener such as a bone fastener. As will be described in greater detail below, bore 142 is sized and shaped to receive and guide a fastener to attach plate 100 to a bone structure. Furthermore, the seat formed by internal surface 116 can be positioned such that a head of a fastener resting in the seat can be positioned at least partially above grooves 126 and 128 and a lower portion of channel 124. Moreover, the seat formed by internal surface 116 can be positioned such that a head of a fastener resting in the seat can be positioned at least partially above the upper surface 102 of plate 100.

With reference to FIGS. 1 and 5, the interface between the proximal portion 110 and distal portion 112 represents a frangible or break-off connection. In that regard, the break-off connection is created by a groove 146 extending about post 106 at the interface between the proximal portion 110 and distal portion 112. The thickness of external surface 114 that forms groove 146 is about 50% to about 60% less thick than the remainder of the thickness of external surface 114. For example, the thickness of the external surface 114 that forms groove 146 is about 0.4 millimeters while the thinnest portion of external surface 114 that forms external threads 118 is about 0.9 millimeters. However, in other embodiments the thickness of external surface 114 that forms groove 146 can range from about 1% to about 99% less thick than the remainder of the thickness of external surface 114.

Additionally, it is further contemplated in alternative embodiment that the proximal portion 110 and the distal portion 112 can be manufactured to be composed of differing materials such that the proximal portion 110 is more susceptible to break-off than the distal portion 112. Furthermore, it is contemplated in an alternative embodiment that the interface forming the break-off connection between the proximal portion 110 and the distal portion 112 can be composed of a different material than that of the proximal portion 110 and/or distal portion 112. In that regard, the break-off connection can be composed of a different material than that of the proximal portion 110 and/or the distal portion 112 such that the proximal portion 110 is more susceptible to break-off from the distal portion 112 along the break-off connection formed of the different material.

As shown in FIGS. 1 and 4, plate 100 has a plurality of apertures 148 within groove 146 that extend through post 106. Apertures 148 further reduce the structural integrity of the interface between the proximal portion 110 and distal portion 112 of post 106. Thus, groove 146 with apertures 148 enable the break-off connection between the proximal portion 110 and the distal portion 112.

It is contemplated in other embodiments that apertures 148 can have various shapes including, but not limited to, circular, elongated, triangular, rectangular, oval, and square. Furthermore, in another alternative embodiment there is a single aperture formed within groove 146 of post 106, instead of a plurality of apertures. Additionally, in another alternative embodiment the break-off connection can be formed by groove 146 alone without the formation of apertures 148. Similarly, in another alternative embodiment the break-off connection is formed of apertures 148 alone without the formation of groove 146.

Figure 6:
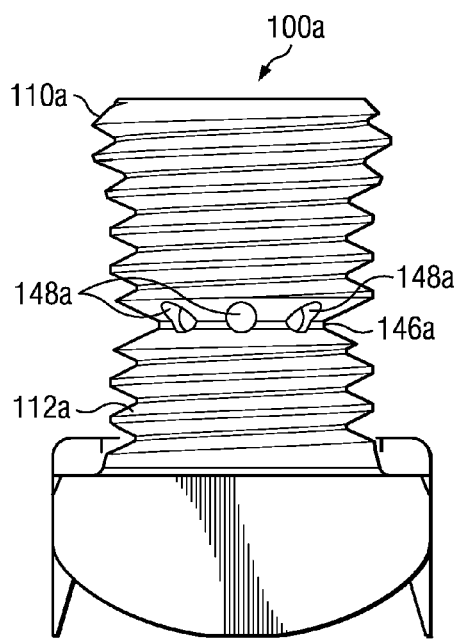
FIG. 6 shows an alternative embodiment of an end view of a plate member having a plurality of apertures within a groove on a side of a post.

Also, in another alternative embodiment there is a plurality of apertures within the groove on either side of the post. FIG. 6 shows an alternative embodiment of an end view of a plate member having a plurality of apertures within the groove on either side of the post. Specifically, FIG. 6 shows plate 100*a* having groove 146*a* in which there is a plurality of apertures 148*a* within the groove on either side of the post. Apertures 148*a* further reduce the structural integrity of the interface between the proximal portion 110*a* and distal portion 112*a* of post 106*a*. Thus, groove 146*a* with apertures 148*a* enable the break-off connection between the proximal portion 110*a* and the distal portion 112*a*.

With reference to plate 100 shown in FIGS. 1-5, the proximal portion 110 and distal portion 112 are designed to provide a clean break from one another through the break-off connection created by groove 146 and apertures 148. The proximal portion 110 and distal portion 112 are separated or broken off from one another by breaking, twisting, rotating, pulling, or otherwise creating stress between the portions at the break-off connection created by groove 146 and apertures 148. For example, a force may be applied to proximal portion 110 in the direction of arrow A1 and an opposing force applied to distal portion 112 in the direction of arrow A2 to shear the proximal portion 110 from the distal portion 112 at groove 146. Torque forces applied to proximal portion 110, in addition to or alternative to shear forces, can also break off the proximal portion 110 from the distal portion 112.

After separating the proximal portion 110 and distal portion 112 from one another, the proximal portion 110 remains a one-piece component, or one-integral portion, even though it is separated from plate 100. In that regard, the proximal portion 110 remains a one-piece component because the external threads 114 extend circumferentially around a proximal end 150 of the proximal portion 110. Therefore, there are no loose portions or particulates of proximal portion 110 upon separating the proximal portion 110 from the distal portion 112 of post 106.

Plate 100 also has an inserter/counter torque feature 152 located on upper surface 102 between posts 106 and 108. Inserter/counter torque feature 152 has tabs 154, 156, and 158 that define grooves 160 and 162, or channels. In particular, tab 156 has a threaded aperture 164 extending through tab 156 to the lower surface 104 of plate 100. Tabs 154, 156, and 158 with channels 160 and 162 define surfaces that enable an instrument to interface with plate 100 for insertion and positioning of the plate along the spinal column. Furthermore, tabs 154, 156, and 158 with channels 160 and 162 define counter torque surfaces that aid in the breaking of the frangible connection between the proximal portion 110 and distal portion 112 of post 106.

Figure 7:
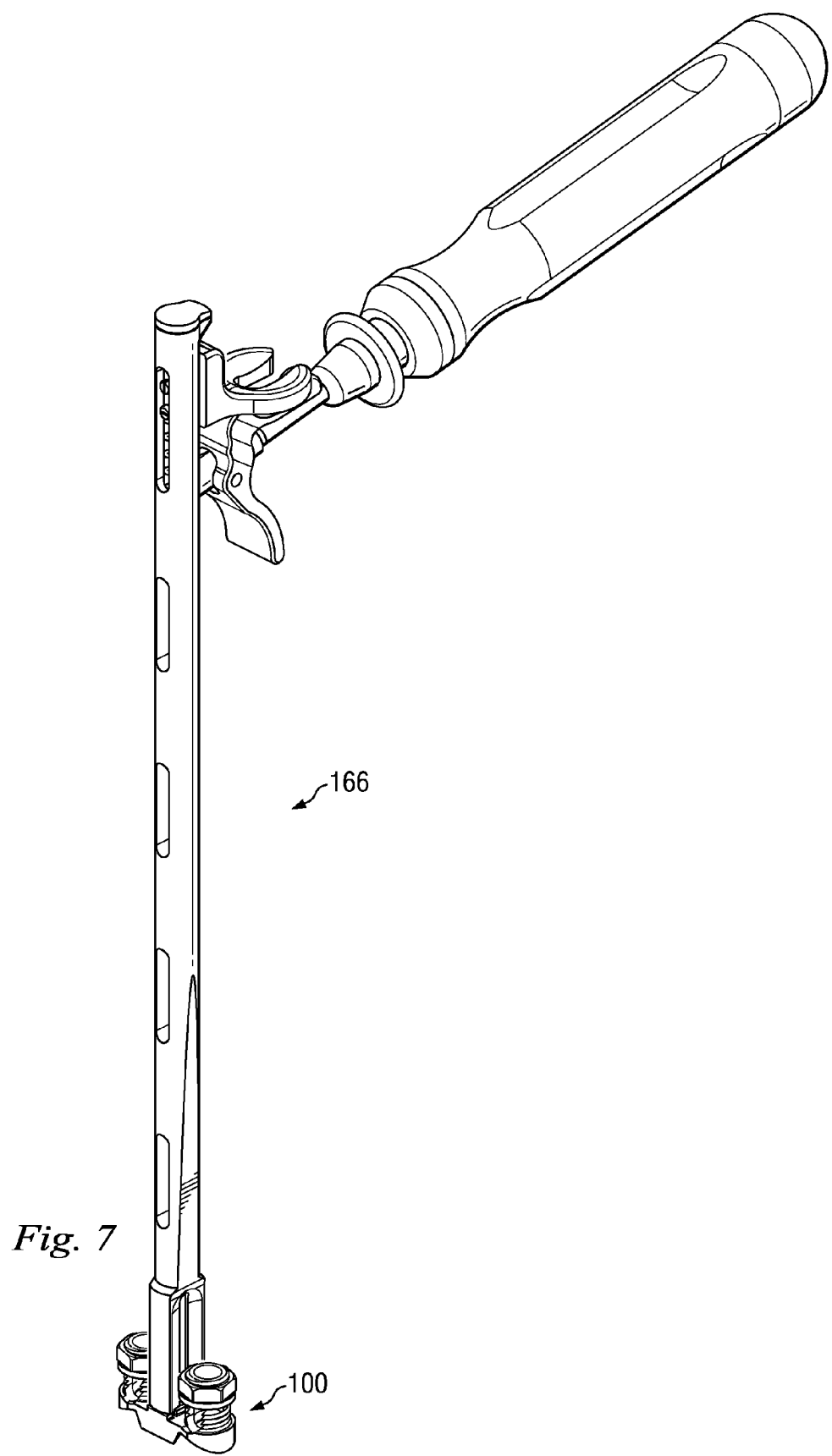
FIG. 7 is a perspective view of an exemplary inserter instrument coupled to the plate of FIG. 1.

FIG. 7 is a perspective view of an exemplary inserter/counter torque instrument coupled to the plate of FIG. 1. As shown, inserter/counter torque instrument 166 engages with plate 100 via tabs 154, 156 (with threaded aperture 164), and 158, and grooves 160 and 162 to provide counter torque surfaces and to aid insertion and positioning of plate 100 along the spinal column. As discussed above, the proximal portion 110 and distal portion 112 are designed to provide a clean break from one another through the break-off connection created by groove 146 and apertures 148. The proximal portion 110 and distal portion 112 are separated or broken off from one another by breaking, twisting, rotating, pulling, or otherwise creating stress between the components at the break-off connection created by groove 146 and apertures 148. Inserter/counter torque instrument 166 can be used to apply counter torque to the plate 100 via engagement with inserter/counter torque feature 152 in the direction of arrow A2 while a force may be applied to proximal portion 110 in the direction of arrow A1 (FIG. 1) to shear the proximal portion 110 from the distal portion 112 at groove 146. As indicated above, torque forces, in addition to or alternative to shear forces, can also break off the proximal portion 110 from the distal portion 112.

Additionally, plate 100 has keels 168 and 170 extending from the lower surface 104. Keels 168 and 170 are positioned along an outer edge of plate 100 and extend at least along a portion of the outer edge of plate 100. As best seen in FIG. 4, keels 168 and 170 have inner surfaces 172 and 174, respectively, that taper towards the outer edge of plate 100. In other embodiments, plate 100 can have more than two keels or a single keel. Keels 168 and 170 are used in part to secure plate 100 to a bone structure and provide stability and resistance to unwarranted movement of plate 100 once affixed to the bone structure.

As best shown in FIG. 5, the lower surface 104 of plate 100 is generally arcuate shaped. In that regard, lower surface 104 can have an undulating or conical geometry in order to provide a better securement to the bone structure in which pate 100 is affixed. In other words, lower surface 104 can be shaped to match the contours of the bone structure to which plate 100 is secured. As shown, plate 100 has an arcuate shape to match an anterior side of a vertebral body. Additionally, lower surface 104 of plate 100 can be coated with bone growth promoting substances in order to provide a better securement to the bone structure in which pate 100 is affixed. However, it is contemplated that any portion of plate 100 can be coated with bone growth promoting substances Furthermore, it is contemplated in an alternative embodiment that plate 100 can have a varied thickness to allow for contour modifications of the plate. For example, in an alternative embodiment plate 100 can have a reduced or thinned thickness between posts 106 and 108 to permit contour modifications of the plate between the posts 106 and 108 such that the contour of the plate accommodates the shape of the bone structure to which plate 100 is affixed.

With reference to FIGS. 1 and 2, plate 100 can engage locking members 176 and 178, or locking nuts. Specifically, locking members 176 and 178 have internal threads 180 and 182, respectively, that engage the external threads 118 of posts 106 and 108. Plate 100 can be preassembled with locking members 176 and 178 already threadedly engaged with posts 106 and 108. Alternatively, plate member 100 can be provided separate from locking members 176 and 178 such that a healthcare provider subsequently threadedly engages the locking members onto the posts of plate 100. As will be discussed in greater detail below, locking members 176 and 178 are used to lock or secure a flexible connection member captured by post 106 and 108 to plate 100.

Figure 8:
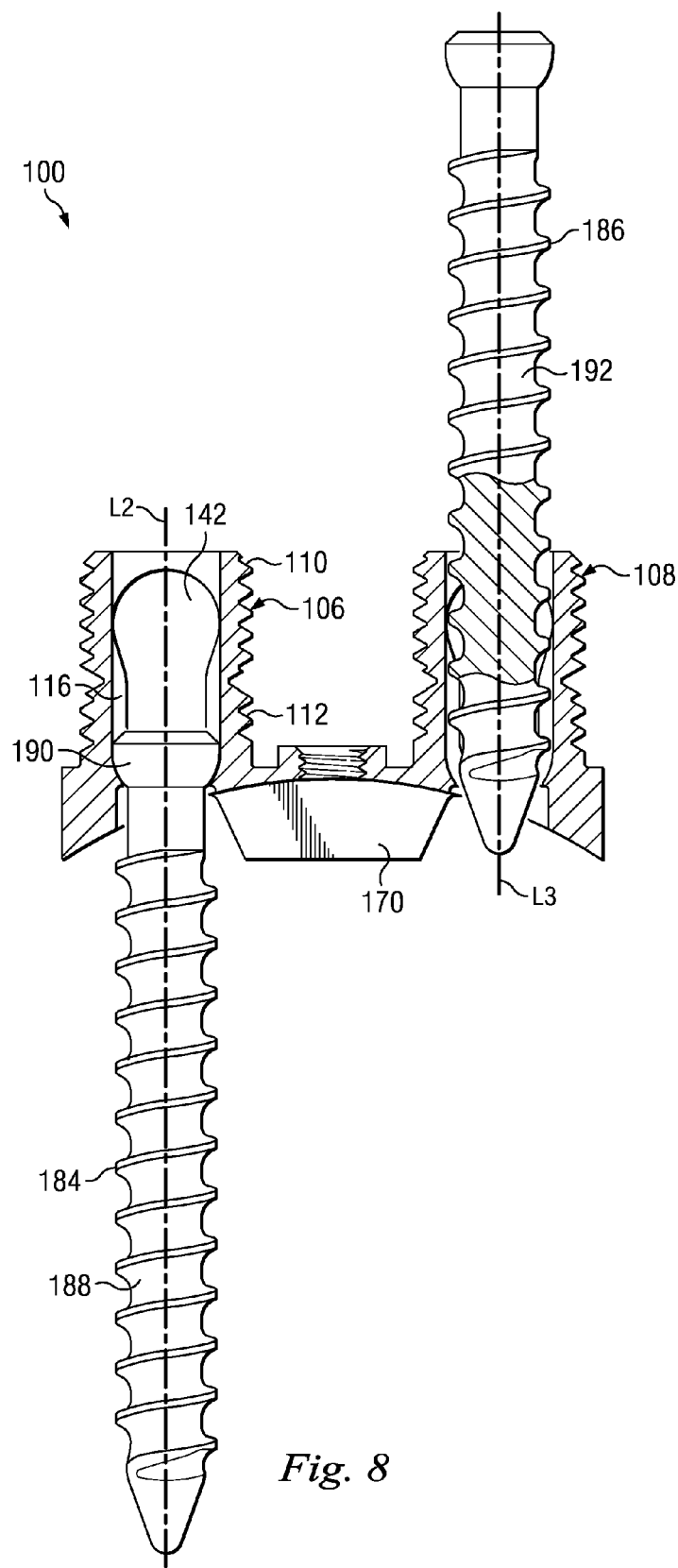
FIG. 8 is a cross-section view of the side view of the plate of FIG. 1 with a pair of bone fasteners being inserted through the plate.

FIG. 8 is a cross-section view of the side view of the plate of FIG. 1 with a pair of bone fasteners being inserted through the plate. As discussed above, bore 142 is sized and shaped to receive and guide a bone fastener to attach plate 100 to a bone structure. As shown, fasteners 184 and 186 are inserted through the proximal openings of posts 106 and 108, respectively. With respect to post 106, shaft portion 188 of fastener 184 has been positioned along axis L2 through bore 142 such that a head 190 of the fastener is fully seated within the seat formed by the internal surface 116 of post 106.

Additionally, FIG. 8 shows shaft 192 of fastener 186 being guided by post 108. In that regard, the diameter of bore 142 is substantially similar to the diameter of shaft 192 such that fastener 186 is guided along an axis L3 as defined by post 108. Thus, posts 106 and 108 act as a guide during the insertion of fasteners within a bone structure by directing and positing fasteners along a desired axis.

It should be noted that axes L2 and L3 in FIG. 8 are substantially parallel to one another. Therefore, posts 106 and 108 are substantially parallel to one another. However, in other embodiments the posts can be angle with respect to one another.

Any fasteners, including bone fasteners, can be used in the embodiments described herein that are suitable for providing a sufficient anchor of the pate into a bone structure. For example, suitable fasteners can include bone screws, staples, nails, anchors coated with bone growth promoting substances, screw-anchor combinations, and the like.

Figure 9:
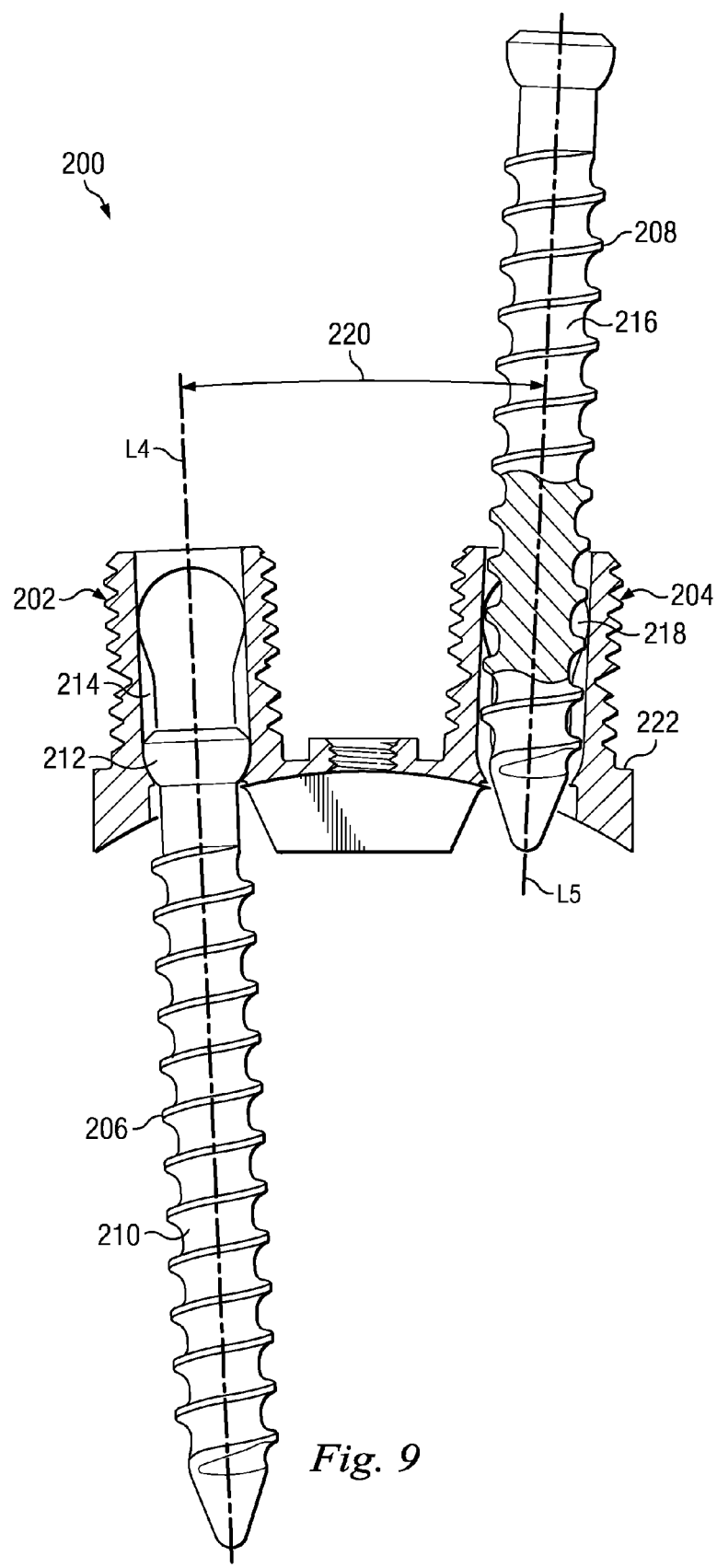
FIG. 9 is a cross-section view of a side view of an alternative embodiment of a plate with a pair of bone fasteners being inserted through the plate according to another embodiment of the present disclosure.

FIG. 9 is a cross-section view of a side view of an alternative embodiment of a plate with a pair of bone fasteners being inserted through the plate according to another embodiment of the present disclosure. As shown, plate 200 has posts 202 and 204 and fasteners 206 and 208 are being inserted through, respectively. With respect to post 202, shaft portion 210 of fastener 206 has been guided and positioned by post 202 along an axis L4 until a head 212 of the fastener is fully seated within the seat formed by the internal surface 214 of post 202. Additionally, FIG. 9 shows shaft 216 of fastener 208 being guided by post 204 along an axis L5. In that regard, the diameter of bore 218 is substantially similar to the diameter of shaft 216 such that fastener 208 is guided along axis L5 as defined by post 204. Thus, posts 202 and 204 act as a guide during the insertion of fasteners within a bone structure by directing and positioning fasteners along a desired axis.

Furthermore, posts 202 and 204 are positioned at an angle 220 with respect to one another. For example, angle 220 can range from about 0° to about 30°. Because the posts 202 and 204 are angled with respect to each other then axes L4 and L5 are angled with respect to one another at angle 220 as well. Furthermore, it is contemplated that axes L4 and L5 can extend at an oblique angle with respect to an upper surface 222 of plate 200. Therefore, fasteners 206 and 208 converge toward one another when inserted into a bone structure through posts 202 and 204. The convergence of fasteners 206 and 208 towards one another when inserted into the bone structure increases the resistance of the fasteners 206 and 208 and plate 200 to being pulled out of the bone structure.

Figure 10:
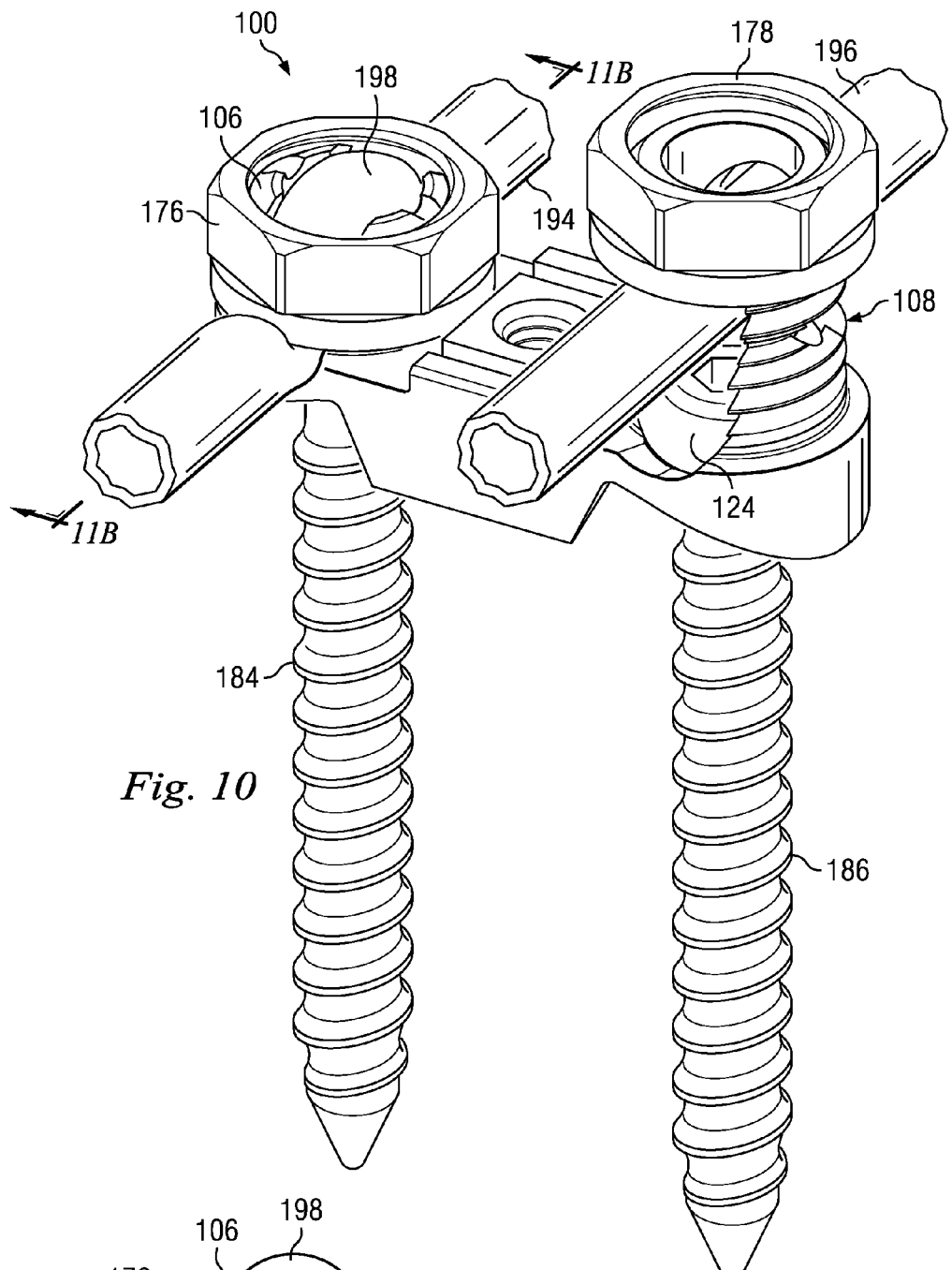
FIG. 10 is a perspective view of the plate of FIG. 1 with a first flexible connection member passing through a first post and a second flexible connection member passing through a second post.
Figure 11B:
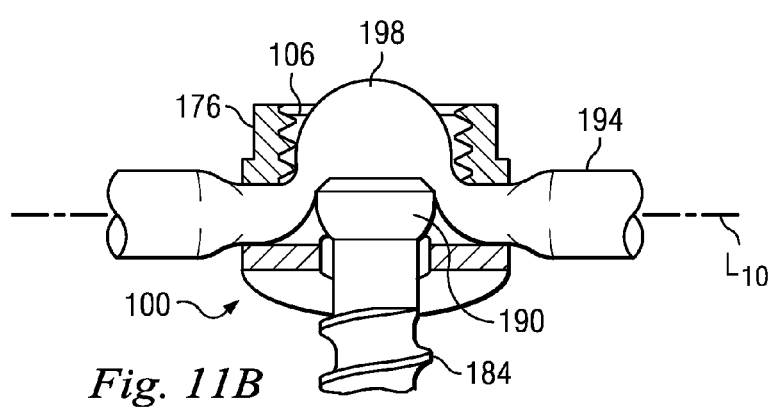
FIG. 11(b) is a cross-section view of an end view of the plate of FIG. 10.
Figure 11A:
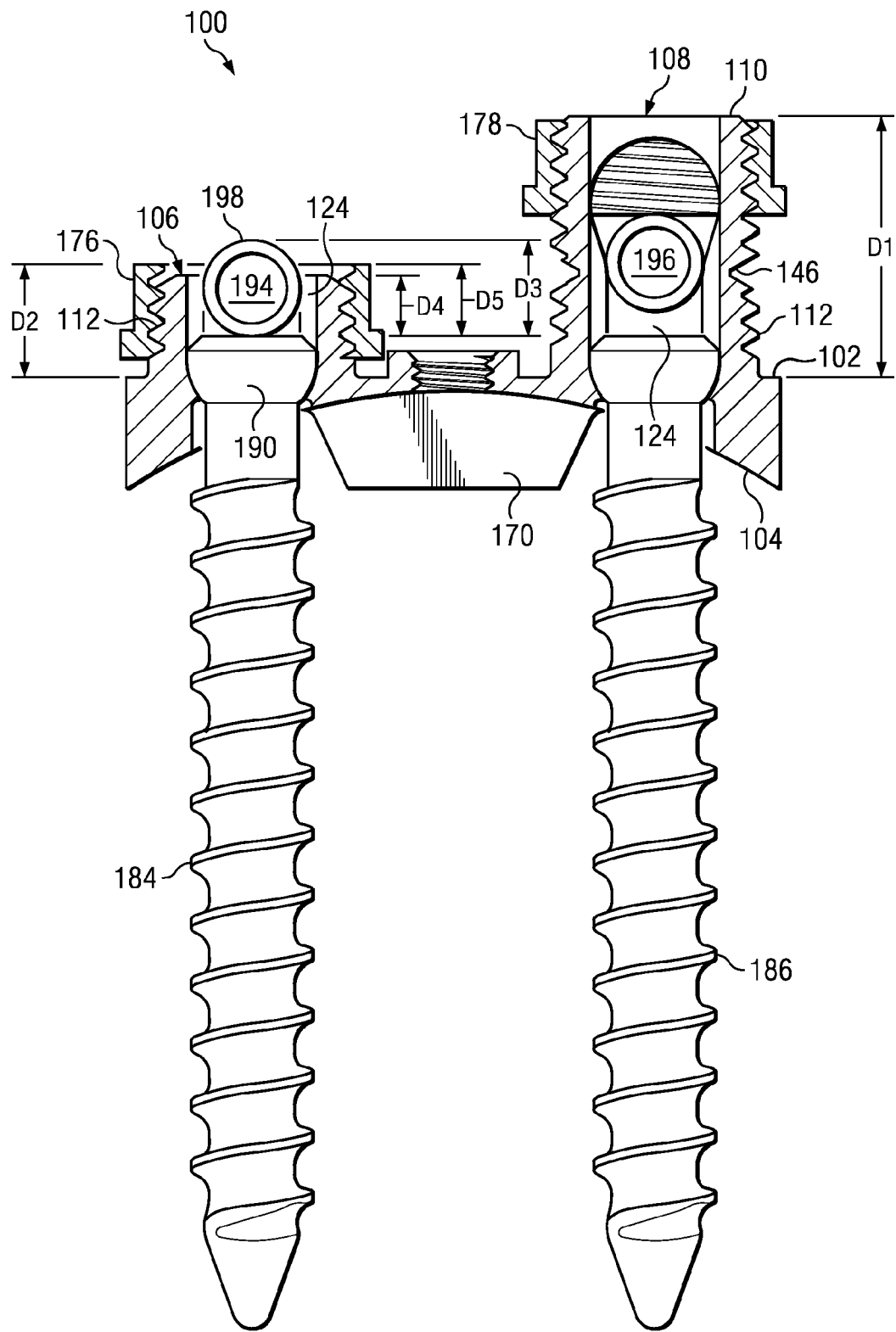
FIG. 11(a) is a cross-section view of a side view of the plate of FIG. 10.

With reference to FIGS. 10, 11(a), and 11(b), the plate of FIG. 1 is shown capturing, or receiving, a flexible connection member. FIG. 10 is a perspective view of the plate of FIG. 1 with a first flexible connection member passing through a first post and a second flexible connection member passing through a second post. FIG. 11(a) is a cross-section view of a side view of the plate of FIG. 10. FIG. 11(b) is a cross-section view of an end view of the plate of FIG. 10.

As shown in FIGS. 10, 11(a), and 11(b), plate member 100 has captured flexible connection members 194 and 196 within posts 106 and 108, respectively. Flexible connection members 194 and 196, or any other flexible connection members disclosed herein, can include, but not limited to, biocompatible ligaments, flexible rods, and tethers similar to those disclosed in U.S. Pat. Nos. 5,092,866, 6,296,643, 6,299,613, 6,551,320, and 6,436,099, the disclosures of which are incorporated by reference herein in their entirety.

As shown in FIGS. 10 and 11(a), flexible connection member 196 is received within channel 124 of post 108. In this state or condition, post 108 can be considered in a first configuration or unlocked with respect to flexible connection member 196. Flexible connection member 196, for example, can rotate, slide, and translate within and through channel 124 of post 108. In other words, flexible connection member 196 can move freely with respect to post 108 when the post is in an unlocked condition.

The first configuration, or unlocked state, of post 108 has many advantages for reception and insertion of flexible connection member 196. Because proximal portion 110 of post 108 has not been separated from distal portion 112 via the break-off connection formed by groove 146 and apertures 148, insertion of flexible connection member 196 through channel 124 is made easier. More specifically, as discussed above with reference to FIG. 5 in association with post 106, post 108 has a key hole shape for channel 124 for receiving the flexible connection member 196 while assuming the first configuration. In that regard, the width W1 of lateral openings 120 and 122 within the proximal portion 110 is wider than their respective opening width W2 within the distal portion of post 108 thereby making it easier to for insertion of flexible connection member 196 through channel 124. Furthermore, proximal portion 110 enables post 108 to extend further axially away from upper surface 102 than without proximal portion 110. In other words, proximal portion 110 enables post 108 to have a taller profile or height (as shown by D1) for receiving flexible connection member 196. Therefore, proximal portion 110 of post 108 aids during reception and insertion of flexible connection member 196 by providing a tall receiving profile with a wide opening. However, as will be discussed below, because proximal portion 110 is separable from distal portion 112, plate 100 has the capability to have a tall profile plate during reception and insertion of a flexible connection member, but transform into an advantageous low profile plate by allowing proximal portion 110 to be separated from the plate.

As shown in FIGS. 10, 11(*a*), and 11(*b*), flexible connection member 194 is received within channel 124 of post 106. Flexible connection member 194 is locked, or rigidly secured to plate 100. In this second configuration, post 106 can be considered locked with respect to flexible connection member 194. In other words, flexible connection member 194 is prevented from relative movement with respect to post 106 when the post is in the locked condition. Furthermore, as will be described in more detail below, because proximal portion 110 has been separated from the distal portion 112 of post 106, channel 124 has a u-shape for receiving the flexible connection member 194 while assuming the second configuration.

Flexible connection member 194 is rigidly secured, or locked, within channel 124 of post 106 via locking member 176. As shown, locking member 176 threadedly engages post 106 such that rotation of locking member 176 about post 106 rigidly secures, locks, compresses, pinches, or crushes flexible connection member 194 between locking member 176 and upper surface 102 of plate 100. Thus, flexible connection member 194 is locked within channel 124 of post 106 via the engagement of locking member 176 upon flexible connection member 194.

The locked configuration of post 106 results in channel 124 having a u-shape for receiving the flexible connection member 194. In that regard, channel 124 can have a smaller diameter than the diameter of the flexible connection member 194 when the locking member 176 rigidly secures, locks, compresses, pinches, or crushes flexible connection member 194 between locking member 176 and upper surface 102 of plate 100. For example, flexible connection member 194 can have a diameter ranging from about 3.0 millimeters to about 4.0 millimeters. Here, for example, flexible connection member 194 can have a diameter of about 3.5 millimeters. By advancement of the locking member 176 along post 106 to rigidly secure the flexible connection member 194 to post 106 the diameter of channel 124 decreases such that the diameter of channel 124 can be less than the diameter of flexible connection member 194. In that regard, the diameter of channel 124 can be less than from about 3.0 millimeters to less than about 4.0 millimeters. Here, for example, channel 124 can have a diameter of less than about 3.5 millimeters. Because the diameter of the flexible connection member 194 is larger than the diameter of channel 124 when post 106 is in the locked configuration, flexible connection member 194 is better secured within channel 124.

It should be noted that the ranges of diameter for flexible connection member 194 and/or any other flexible connection member disclosed herein are for exemplary purpose only. In that regard, the flexible connection member can have larger or smaller diameters than discloses herein. Accordingly, the diameters of channels defined the posts described herein can be sized to accommodate the range of possible diameters for the flexible connection members, including having diameters larger than or smaller than the diameter of the flexible connection members disclosed herein.

Furthermore, locking member 176 rigidly secures, locks, compresses, pinches, or crushes flexible connection member 194 between locking member 176 and head 190 of fastener 184. Because the seat portion of bore 142 causes the head 190 of fastener 184 to at least partially sit above grooves 126, 128 and the lower portion of channel 124 and/or upper surface 102, a kink 198, or deformation, along flexible connection member 194 is formed when the locking member 176 engages the flexible connection member 194. Kink 198 increases resistance to movement of flexible connection member 194 along axis L1 (FIG. 1). Additionally, kink 198 prevents fastener 184 from backing out of post 106 by exerting an axial force against head 190 of fastener 184 when locking member 176 locks the flexible connection member 194 between locking member 176 and upper surface 102 of plate 100.

Furthermore, as shown in FIG. 11(*b*), kink 198 non-linearly passes through channel 124 when the flexible connection member is rigidly secured to plate 100. In that regard, flexible connection member 194 extends linearly along an axis L10. However, when post 106 is in the locked configuration channel 124 defines a non-linear passage for reception of flexible connection member 194. The non-linear passage is non-linear with respect to axis L10. Therefore, kink 198 of flexible connection member 194 non-linearly extends through the non-linear passage defined by channel 124 when the post is in the locked configuration.

It should be noted in other alternative embodiments that flexible connection member 194 extends linearly through channel 124 when the post 106 is in the locked configuration. For example, in such an alternative embodiment the head of a fastener can be reduced in diameter and/or the seat portion defined by internal surface 116 can be positioned such that the head of the fastener is at or below the upper surface 102 of plate 100 thereby providing a linear passage through channel 124.

As shown in FIG. 11(*a*), kink 198, or deformation, extends a distance D3 from the top surface of head 190 of fastener 184 when the flexible connection member 194 is rigidly secured to plate 100. In that regard, distance D3 can range from about 3.0 millimeters to about 4.0 millimeters. For example, here distance D3 is about 3.5 millimeters. Moreover, in alternative embodiments distance D3 can rage from about 0.1 millimeters to about 4.0 millimeters.

Additionally, as shown in FIG. 11(*a*), a top surface of distal portion 112 extends a distance D4 from the top surface of head 190 of fastener 184 when the flexible connection member 194 is rigidly secured to plate 100. In that regard, distance D4 can range from about 1.0 millimeters to about 2.0 millimeters. For example, here distance D4 is about 1.5 millimeters. Moreover, in alternative embodiments distance D4 can rage from about 0.1 millimeters to about 2.0 millimeters.

Furthermore, as shown in FIG. 11(*b*), a top surface of locking member 176 extends a distance D5 from the top surface of head 190 of fastener 184 when the flexible connection member 194 is rigidly secured to plate 100. In that regard, distance D5 can range from about 1.5 millimeters to about 2.5 millimeters. For example, here distance D5 is about 2.1 millimeters. Moreover, in alternative embodiments distance D5 can rage from about 0.1 millimeters to about 2.5 millimeters.

Therefore, as shown in FIGS. 11(*a*) and 11(*b*), kink 198 is positioned above the top surfaces of the distal portion 112 and locking member 176. As mentioned above, this positioning of kink 198 increases resistance to movement of flexible connection member 194 along axis L1 (FIG. 1) and prevents fastener 184 from backing out of post 106.

Although distances D4 and D5 are shown having different overall measurements, it is contemplated that D4 and D5 can be configured such that D4 is equal to or greater than D5. In other words, the top surface of distal portion 112 can be flush, or coplanar, with a top surface of locking member 176 when D4 equals D5 and the top surface of distal portion 112 can extend above the top surface of locking member 176 when D4 is greater than D5.

Furthermore, because the receiving members (e.g. posts 106 and 108) for the flexible connection members (e.g. 194 and 196) are part of plate member 100 this allows a fastener to be fully seated within the seat of bore 142. This is an important feature because plate 100 can be part of a non-fusion system that enables the spinal column to retain mobility. In that regard, a fastener fully seated within plate 100 provides better wherewithal to secure plate 100 to a vertebral body undergoing the continuous stress placed on plate 100 and the fastener by the motion of the spine.

A fastener is able to fully sit within the seat of bore 142 because the receiving members (e.g. posts 106 and 108) are positionable independent of the fastener. Therefore, a healthcare provider utilizing plate 100 only has to orient the receiving members with respect to the flexible connection member passing through channel 124. Thus, a fastener can be positioned through bore 142 independent of the orientation between the plate and the flexible connection member thereby allowing the fastener to be fully seated within plate 100.

It should be note that although posts 106 and 108 have been described in a locked or second configuration and an unlocked or first configuration, respectively, either post may assume the first and second configurations. In other words, posts 106 and 108 can both be in a first configuration (e.g. unlocked) or a second configuration (e.g. locked). Additionally, post 108 can be in a second configuration (e.g. locked) while posts 106 is in a first configuration (e.g. unlocked), or vice versa.

A plate with a tall profile is typically needed when a larger flexible connection member, such as a tether having a circular cross section, is used in order to provide a taller receiving structure to capture the larger flexible connection member. However, a tall profile plate can present problems for use in a patient's body especially along the anterior portion of the spinal column. Plate 100 addresses this problem by providing a plate that can have a tall profile and a low profile. Specifically, as shown in FIG. 11(a), plate 100 has a tall profile when proximal portion 110 is attached to the plate 100 (e.g. post 108) and a low profile plate when proximal portion 110 is separated from plate 100 (e.g. post 106).

With reference to FIG. 11(a), as previously mentioned, post 108 extends axially from the upper surface 102 by the distance D1. Here, distance D1 is about 14 millimeters. However, in other embodiments distance D1 can range from about 8 millimeters to about 20 millimeters. Furthermore, it is contemplated that the distance D1 can be any distance in order to accommodate the passage of plate 100 within and around any anatomical structure of a patient's body.

By contrast, post 106 extends axially from the upper surface 102 by a distance D2. Distance D2 is less than distance D1 because proximal portion 110 of post 106 has been removed via the break-off connection formed by groove 146 with apertures 148. In other words, D2 represents the axial extending height of the distal portion 112 that remains after removal of the proximal portion 110. Here, distance D2 is about 4 millimeters. However, in other embodiments distance D2 can range from about 2 millimeters to about 6 millimeters. Furthermore, it is contemplated that the distance D2 can be any distance in order to accommodate the passage of plate 100 within and around any anatomical structure of a patient's body.

Therefore, the profile of plate 100 can be changed via the break-off connection. Specifically, posts 106 and 108 can extend axially from the upper surface 102 by the distance D1 in order to provide a tall profile for receiving a flexible connection member, such as a round or circular tether. Then after reception of the flexible connection member the plate 100 can assume a low profile by removing proximal portion 110 from plate 100 via the break-off connection described above. The low profile for plate 100 accommodates the anatomy of a patient's body, especially along the anterior spinal column.

By way of example, and not limitation, the height of posts 106 and 108 can be reduced about 50% to about 70% by the break-off connection. In other words, distance D2 is about 50% to about 70% less than distance D1. However, in other embodiments the height of posts 106 and 108 can be reduced about 20% to about 90%. Still further, it is contemplated that the break-off connection can be formed along any portion of either posts 106 and 108 such that height of posts 106 and 108 can be reduced by any specified amount in order to accommodate the anatomy of a patient's body.

Additionally, as best shown in FIG. 3, plate 100 has generally elliptical shape geometry. The elliptical shape geometry of plate 100, for example, and not by way of limitation, allows for an easier passage through a patient's rib cage during a lateral approach to the spinal column.

Even though reference to the elliptical shape geometry of plate 100 has been mentioned as advantageous to a lateral surgical approach, it is still contemplated within the scope of this disclosure that any surgical approach can be used with plate 100 or any other embodiments disclosed herein. For example, the plates disclosed herein can be used in a posterior, lateral, and/or anterior approach to a patient's spinal column.

Figure 12:
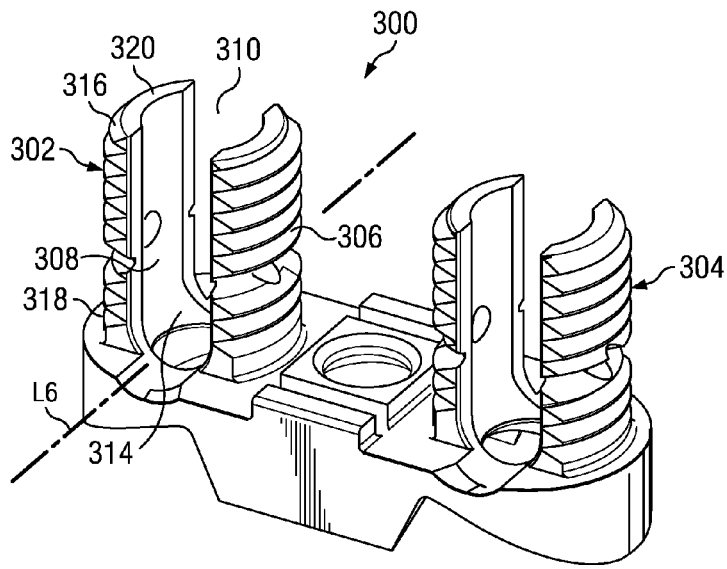
FIG. 12 is an alternative embodiment of a plate for attachment to a bone structure according to another embodiment of the present disclosure.
Figure 13:
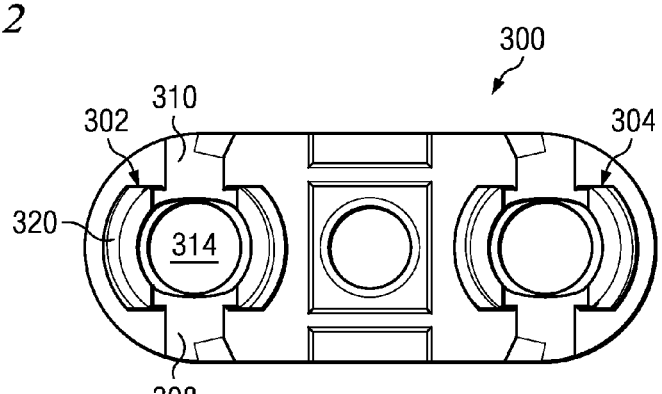
FIG. 13 is an overhead view of the plate of FIG. 12.

FIGS. 12 and 13 show an alternative embodiment of a plate for attachment to a bone structure. FIG. 12 is a perspective view of the alternative embodiment. FIG. 13 is an overhead view of the plate of FIG. 12.

Plate 300 has features similar to those described above with respect to plate 100. For brevity purposes, those features will not be described with respect to plate 300. Furthermore, features described with respect to any embodiment disclosed herein can also be incorporated to any other embodiments.

Plate 300 has posts 302 and 304. Posts 302 and 304 have the same features. Therefore, the description of post 302 is applicable for post 304. Accordingly, like reference numerals are shown in the drawings to denote similar features. However, features of post 304 will not be separately described herein.

Post 302 has external threads 306 that are interrupted and truncated to form lateral openings 308 and 310 along an external surface 312 of post 302. Lateral openings 308 and 310 provide access to a channel 314, or a slot, extending through post 302 along an axis L6. As shown in FIG. 13, lateral openings 308 and 310 are in alignment with one another along axis L6. Lateral openings 308 and 310 are u-shape thereby making channel 314 generally u-shape as well. As shown, lateral openings 308 and 310 extend from a proximal portion 316 to a distal portion 318 of post 302.

Lateral openings 308 and 310 as well as channel 314 allow plate 300 to capture, or receive, a flexible connection member. In that regard, because lateral openings 308 and 310 extend to a proximal end 320 of post 302, proximal end 320 is not circumferentially surrounded by external threads 306. Therefore, a flexible connection member can be captured by post 302 through proximal end 320 by positioning the tether parallel to axis L6 in order to capture the tether within channel 314. Additionally, a tether can be captured by post 302 via translating the tether along axis L6 through lateral openings 308 and 310 to capture the tether within channel 314.

Figure 14:
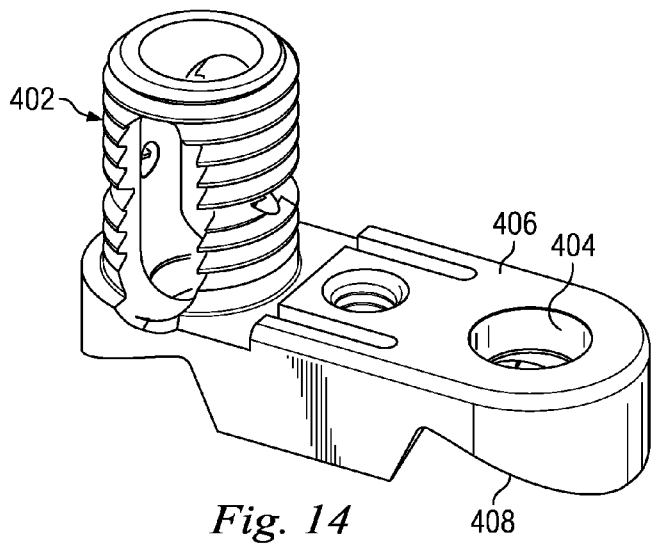
FIG. 14 is an alternative embodiment of a plate for attachment to a bone structure according to another embodiment of the present disclosure.

FIG. 14 is an alternative embodiment of a plate for attachment to a bone structure according to another embodiment of the present disclosure. Plate 400 has features similar to those described above with respect to plate 100. For brevity purposes, those features will not be described with respect to plate 400. Furthermore, features described with respect to any embodiment disclosed herein can also be incorporated to any other embodiments.

Plate 400 has a single post 402. Post 402 has the same features described above with respect to post 106. Although not shown, in an alternative embodiment post 402 has the same features described above for post 302 of plate 300.

In lieu of a second post, plate 400 has an aperture 404. Aperture 404 extends from an upper surface 406 of plate 400 through to a lower surface 408 of plate 402. A fastener, such a fastener 184 described above, can be inserted through aperture 404 to secure plate 400 to a bone structure. Although not shown, one skilled in the art can recognize that a retaining ring or any other type of locking mechanism can be inserted within or around aperture 404 and/or fastener 184 to prevent the fastener from backing out of the aperture.

Figure 15:
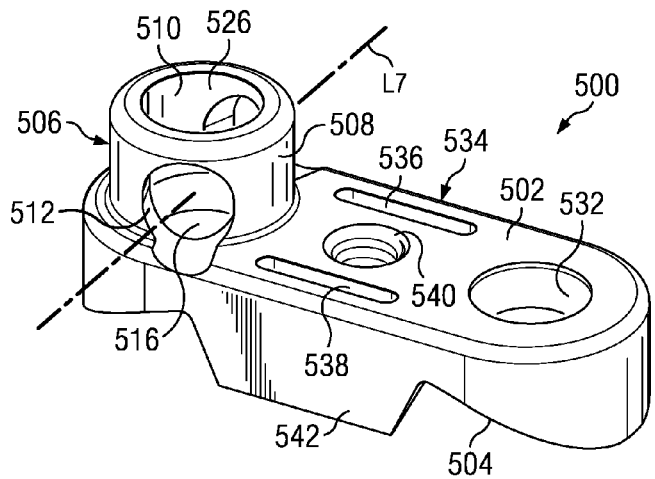
FIG. 15 is an alternative embodiment of a plate for attachment to a bone structure according to another embodiment of the present disclosure.
Figure 16:
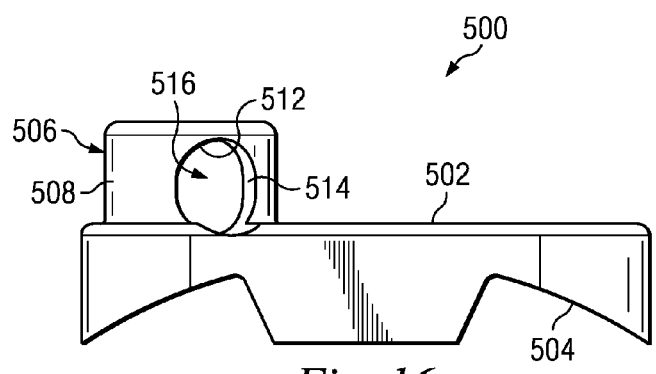
FIG. 16 is a side view of the plate of FIG. 15.
Figure 17:
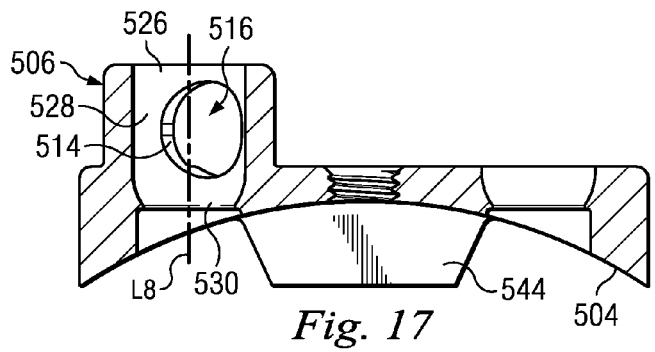
FIG. 17 is a cross-section view of the side view of the plate of FIG. 16.
Figure 19:
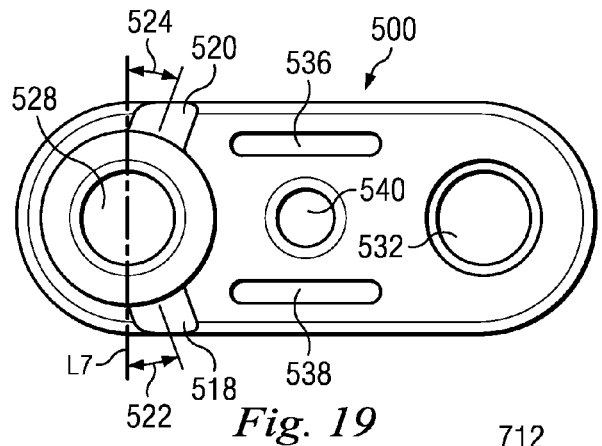
FIG. 19 is an overhead view of the plate of FIG. 15.

FIGS. 15-17 and 19 show an alternative embodiment of a plate for attachment to a bone structure according to another embodiment of the present disclosure. FIG. 15 is a perspective view of the alternative embodiment of the plate. FIG. 16 is a side view of the plate of FIG. 15. FIG. 17 is a cross-section view of a side view of the plate of FIG. 16. FIG. 19 is an overhead view of the plate of FIG. 15.

Referring first to FIG. 15, a perspective view of a plate 500 for attachment to a bone structure, such as a vertebral body of a spinal column, is shown. Plate 500 has an upper surface 502 and a lower surface 504. A post 506, or receiving member, extends axially from the upper surface 502.

Post 506 has an external surface 508 and an internal surface 510. The external and internal surfaces 508 and 510 are interrupted to form lateral openings 512 and 514. Lateral openings 512 and 514 provide access to a channel 516 extending through post 106 at an angle with respect to an axis L7. As shown in FIG. 16, lateral openings 512 and 514 are not aligned with one another. In that regard, lateral openings 512 and 514 are offset from each other and are non-aligned with respect to axis L7.

As best seen in FIGS. 16 and 17, lateral openings 512 and 514 and thereby channel 516, extend below upper surface 502. As shown in FIG. 19, radially extending from the lateral openings 512 and 514 are grooves 518 and 520, or recesses, that are formed within upper surface 502. Grooves 518 and 520 extend at angles 522 and 524, respectively, with respect to axis L7. Angles 522 and 524 can range from about 0° to about 30° with respect to axis L7. As shown, angles 522 and 524 are about 30°, respectively.

Therefore, grooves 518 and 520 allow a flexible connection member received within channel 516 to extend through lateral openings 512 and 514 at angles ranging from about 0° to about 30° with respect to axis L7. It should be noted that angles 522 and 524 can be selected base on anatomical features and spinal deformities of a specific patient. In other words, depending on the type of spinal deformity, a plate having a specified angle for grooves 522 and/or 524 can be selected to correct the deformity.

With reference to FIGS. 15 and 19, post 506 has a proximal opening 526 leading into a bore 528. Bore 528 is sized and shaped to receive and guide a fastener to attach plate 500 to a bone structure. Bore 528 is defined by internal surface 510 and extends along an axis L8. Internal surface 510 tapers near distal opening 530 to form a seat for accommodating a fastener, such as a head of a bone screw. Bore 528 intersects channel 516. Bore 528 terminates at a distal opening 530.

Upper surface 502 of plate 500 also has an aperture 532. Aperture 532 extends through plate 500 from the upper surface 502 to the lower surface 504 of plate 500. A fastener, such as fastener 184 described above, can be inserted through aperture 532 to secure plate 500 to a bone structure. Although not shown, one skilled in the art can recognize that a retaining ring or any other type of locking mechanism can be inserted within or around aperture 532 and/or fastener 184 to prevent the fastener from backing out of the aperture.

It should be noted that in alternative embodiment, plate 500 can be configured with a second post similar to post 506 positioned over aperture 532. In this alternative embodiment, a second flexible connection member can be attached to plate 500 via the second post.

Plate 500 also has an inserter/counter torque feature 534 located on upper surface 502 positioned between post 506 and aperture 532. Inserter/counter torque feature 534 has grooves 536 and 538, or channels, and a threaded aperture 540 extending through plate 500 from the upper surface 502 to the lower surface 504 of plate 500. Grooves 536 and 538 and threaded aperture 540 define surfaces that enable an instrument to interface with plate 500 for insertion and positioning of the plate along the spinal column. Additionally, grooves 536 and 538 and threaded aperture 540 define counter torque surfaces.

Additionally, plate 500 has keels 542 and 544 extending from the lower surface 504. Keels 542 and 544 are positioned along an outer edge of plate 500 and extend at least along a portion of the outer edge of plate 500. In other embodiments, plate 500 can have more than two keels or a single keel. Keels 542 and 544 are used in part to secure plate 500 to a bone structure and provide stability and resistance to unwarranted movement of plate 500 once affixed to the bone structure.

As best shown in FIG. 17, the lower surface 504 of plate 500 is generally arcuate shaped. In that regard, lower surface 504 can have an undulating or conical geometry in order to provide better secure the plate to the bone structure. In other words, lower surface 504 is shaped to match the contours of the bone structure to which plate 500 is secured. As shown, plate 500 has an arcuate shape to match an anterior side of a vertebral body.

Plate 500 is advantageous in allowing a flexible connection member to pass through channel 516 without being compressed and/or crushed. Instead, as described above, plate 500 allows a flexible connection member to be positioned through lateral openings 512 and 514 and into channel 516 at a range of angles, including but not limited, to about 0° to about 30°. Therefore, plate 500 can be a guide used to position the flexible connection member at a specified angle along the spinal column. Thus, plate 500 allows a flexible connection member to translate through channel 516 at various angles without compressing or crushing the tether.

Post 506, as shown in FIG. 17, is integrally formed with upper surface 502 of plate 500. However, in other alternative embodiments, the post is not integrally formed with the upper surface 502 or any other portion of plate 500. For example, in an alternative embodiment the post can translate with respect to upper surface 502 or any other portion of plate 500.

Figure 18:
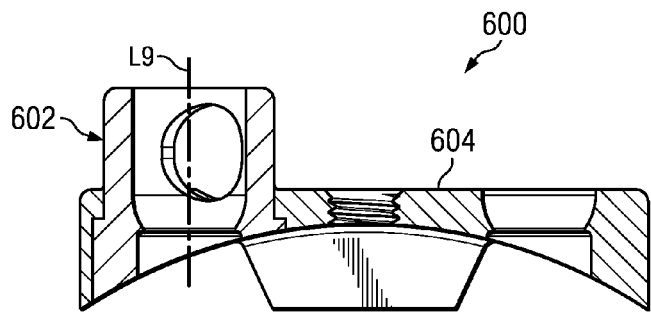
FIG. 18 is a cross-section view of a side view of an alternative embodiment of a plate for attachment to a bone structure according to another embodiment of the present disclosure.

FIG. 18 is a cross-section view of a side view of an alternative embodiment of a plate for attachment to a bone structure according to another embodiment of the present disclosure. As shown in FIG. 18, plate 600 has a post 602 that is not integrally formed with an upper surface 604 or any other portion of plate 600. In this embodiment, because post 602 is not integrally formed with upper surface 604 or any other portion of plate 600, post 602 is capable of rotating about the posts axis L9. The post 602 can rotate from about 0° to about 360° about axis L9. However, in another embodiment the range of rotation for post 602 about its axis can be limited to a specified range anywhere between 0° to 360°.

The ability of post 602 to rotate about axis L9 enables a healthcare provider to make finer adjustments of the post relative to a flexible connection member that may pass through the channel defined by the post. In that regard, the channel and/or openings into the channel can be aligned with the flexible connection member prior to and/or after securement of plate 600 to a bone structure by rotation of post 602. In other words, rotation of post 602 allows a greater degree of alignment possibilities between post 602 and a flexible connection member. In fact, because post 602 rotates it can more evenly distribute tensional forces applied by a flexible connection member received through post 602. In that regard, post 602 can rotate to a given point about axis L9 where the tensional forces applied by a flexible connection member are evenly distributed across post 602. Therefore, rotation of post 602 about axis L9 allows for a greater degree of freedom in alignment of a flexible member with respect to post 602 as well as a more even distribution of tension across post 602 being applied by a flexible connection member captured by post 602.

Figure 20:
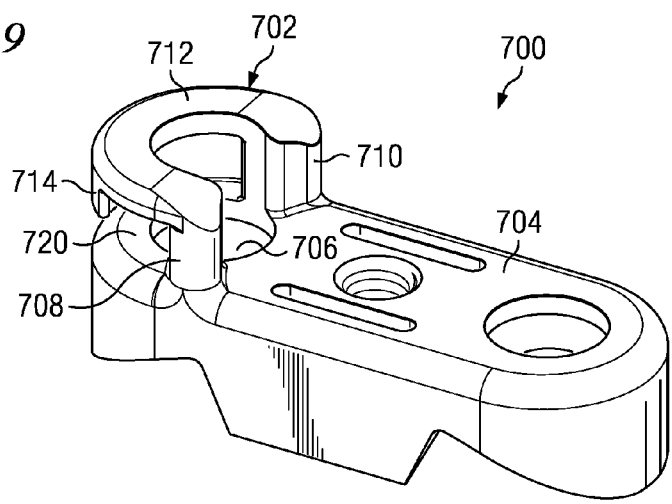
FIG. 20 is an alternative embodiment of a plate for attachment to a bone structure according to another embodiment of the present disclosure.
Figure 21:
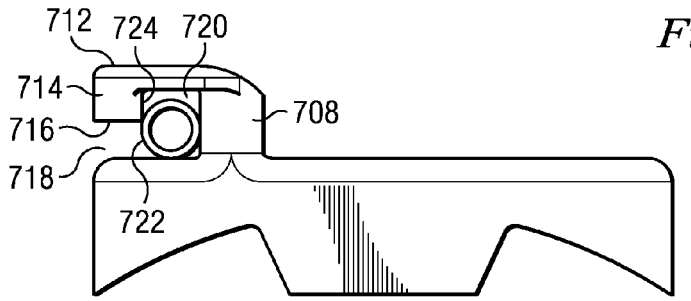
FIG. 21 is a side view of the plate of FIG. 20.
Figure 22:
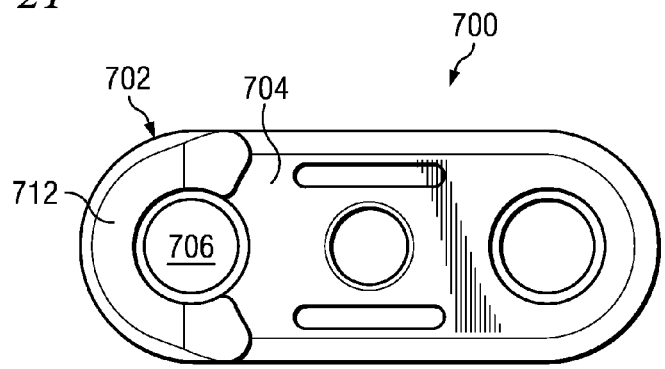
FIG. 22 is an overhead view of the plate of FIG. 20.

FIGS. 20-22 show an alternative embodiment of a plate for attachment to a bone structure according to another embodiment of the present disclosure. FIG. 20 is a perspective view of the alternative embodiment of the plate. FIG. 21 is a side view of the plate of FIG. 20. FIG. 22 is an overhead view of the plate of FIG. 20.

Plate 700 has features similar those described above with respect to plate 500. For brevity purposes, those features will not be described with respect to plate 700. Furthermore, features described with respect to any embodiment disclosed herein can also be incorporated to any other embodiments.

Plate 700 has a post 702 (or receiving member), or hook, extending for an upper surface 704. Post 702 surrounds at least a portion of aperture 706 that is formed in upper surface 704. A fastener, such as fastener 184 described above, can be inserted through aperture 706 to secure plate 700 to a bone structure. Although not shown, one skilled in the art can recognize that a retaining ring or any other type of locking mechanism can be inserted within or around aperture 706 and/or fastener 184 to prevent the fastener from backing out of the aperture.

Post 702 is formed of base sections 708 and 710 with a cantilevered arc section 712 extending between the base projections. Cantilevered arc section 712 substantially matches the curvature of aperture 706 such that section 712 does not cover the aperture. Additionally, the cantilevered arc shaped section 712 has a projection 714 extending along an outer edge of section 712. Projection 714 extends radially toward the upper surface 704 such that a distal end 716 of projection 714 remains spaced apart from the upper surface 704 to define a side opening 718 into a channel 720 defined by post 702.

Post 702 allows a flexible connection member to be side loaded through side opening 718 into channel 720. In that regard, a flexible connection member can be positioned adjacent side opening 718 and hooked or positioned under the distal end 716 of projection 714 to access channel 720. As shown in FIG. 21, once a flexible connection member 722 is positioned within channel 720, internal surface 724 of projection 714 prevents the flexible connection member 722 from falling out of or being removed from channel 720 through side opening 718. Additionally, the flexible connection member 722 in channel 720 contributes to preventing a fastener positioned through aperture 706 to secure plate 700 to a bone structure from backing out of the aperture.

In an alternative embodiment, base sections 708 and 710 of post 702 can be positioned around aperture 706 such that channel 720 has a width that allows a flexible connection member positioned within channel 720 adjacent base sections 708 and 710 to not cover the head of a fastener positioned within aperture 706. In other words, the flexible connection member can be positioned within channel 720 in this alternative embodiment such that a healthcare provider can gain access to the head of a fastener positioned within aperture 706. In such an embodiment, a retaining ring or any other type of locking mechanism can be used to prevent the fastener from backing out of the aperture.

FIGS. 23(a)-(h) show the plate embodiments described herein attached to exemplary spinal columns in various configurations. As shown in FIGS. 23(a)-(h), at least five vertebrae ($V_1$, $V_2$, $V_3$, $V_4$, and $V_5$) are instrumented with an ensemble of plate members, described in FIGS. 1-22, that are linked via flexible connection members $C_1$, $C_2$, and/or $C_3$. These various configurations provide a system for treating a spinal deformity in a skeletally mature or immature spine. More specifically, the plates disclosed herein allow the flexible connection members $C_1$, $C_2$, and/or $C_3$ to constrain spinal growth (in the immature spine) or alter curvature of the spine (in the mature spine).

As discussed above, flexible connection members $C_1$, $C_2$, and $C_3$, or any other flexible connection members disclosed herein, can include, but not limited to, biocompatible ligaments, flexible rods, and tethers similar to those disclosed in U.S. Pat. Nos. 5,092,866, 6,296,643, 6,299,613, 6,551,320, and 6,436,099, the disclosures of which are incorporated by reference herein in their entirety.

As shown in FIGS. 23(a)-(h), a plate member is secured to each of the vertebra via at least one fastener. Furthermore, at least one flexible connection member $C_1$, $C_2$, and/or $C_3$ is positioned through each of the channels of the respective plates to thereby link the plates together. As shown throughout FIGS. 23(a)-(h), the flexible connection members $C_1$, $C_2$, and/or $C_3$ extend between adjacent plate members at various angles and/or are in substantially alignment with each other such that flexible connection member is substantially not angled between adjacent plate members. In other words, it is contemplated that flexible connection members $C_1$, $C_2$, and/or $C_3$ extend between adjacent plate members at various angles or at no angle.

Figure 23C:
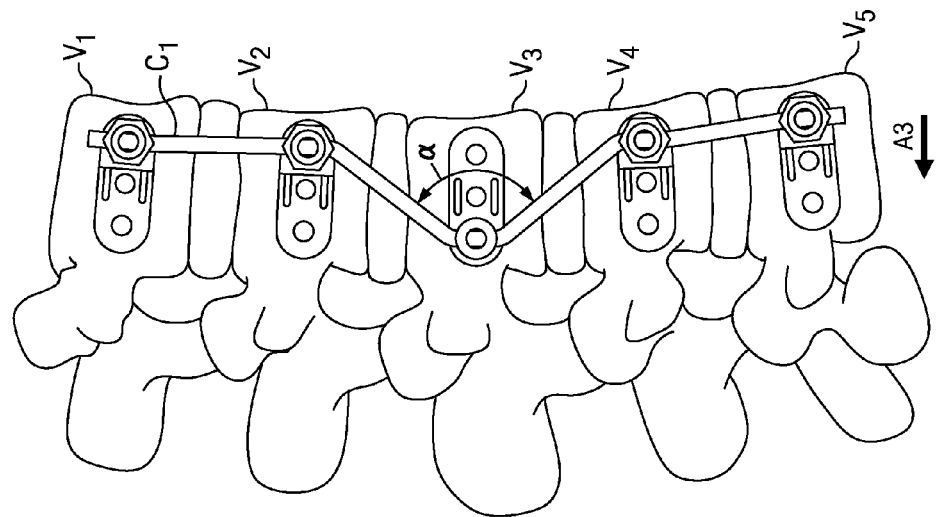
FIGS. 23(a)-(h) show the plate embodiments described herein attached to exemplary spinal columns in various configurations.
Figure 23B:
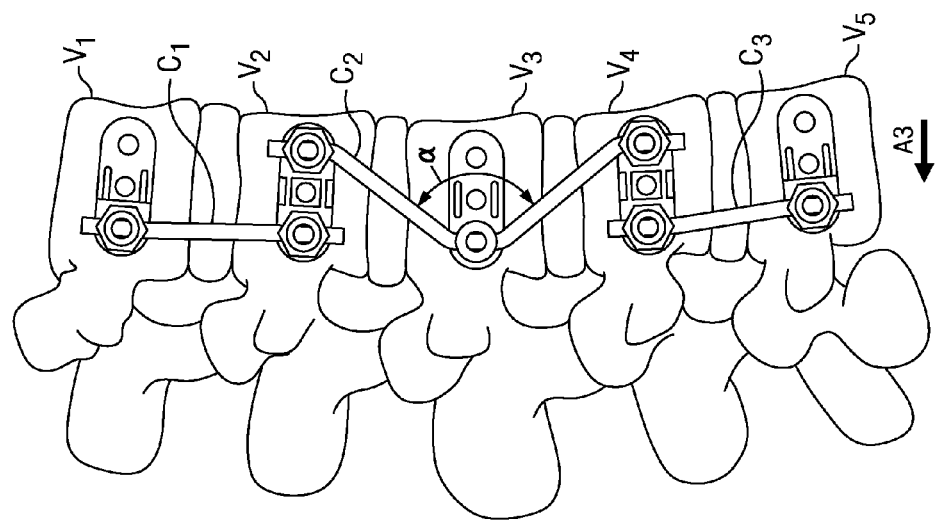
Figure 23A:
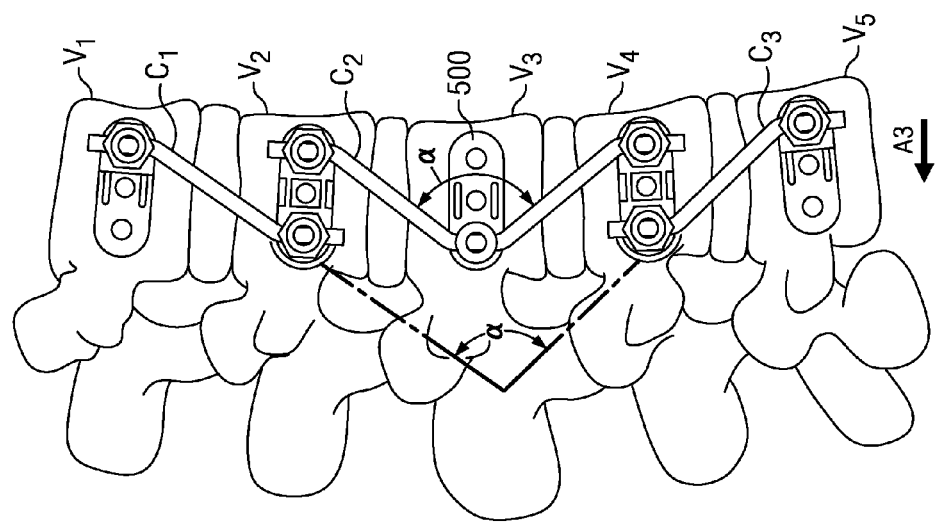
Figure 23F:
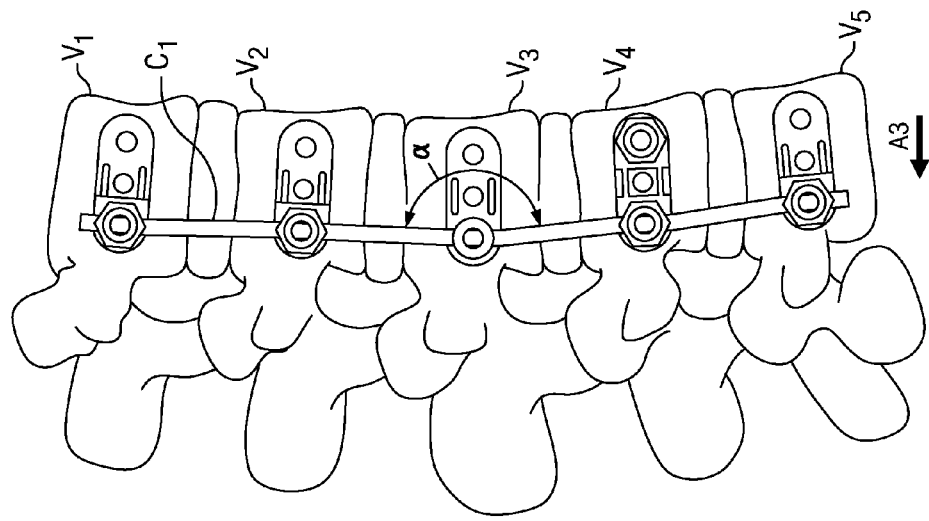
Figure 23E:
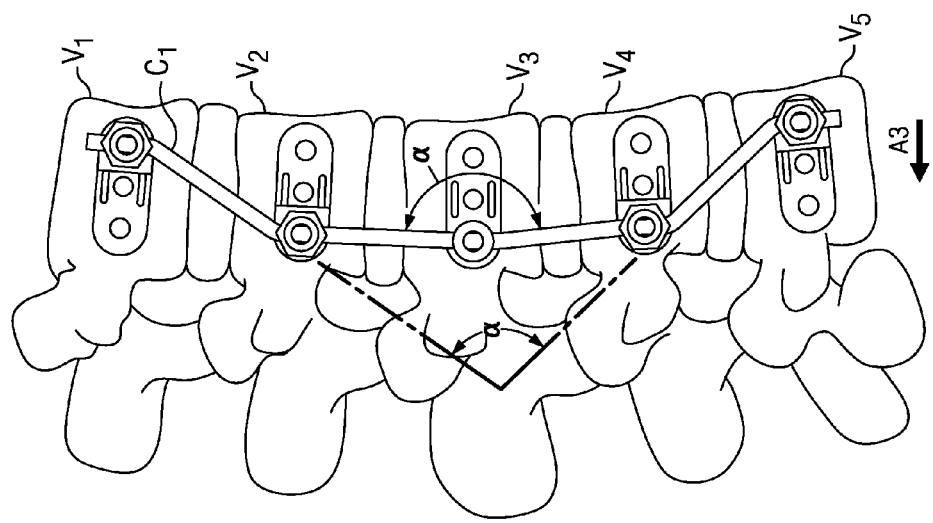
Figure 23D:
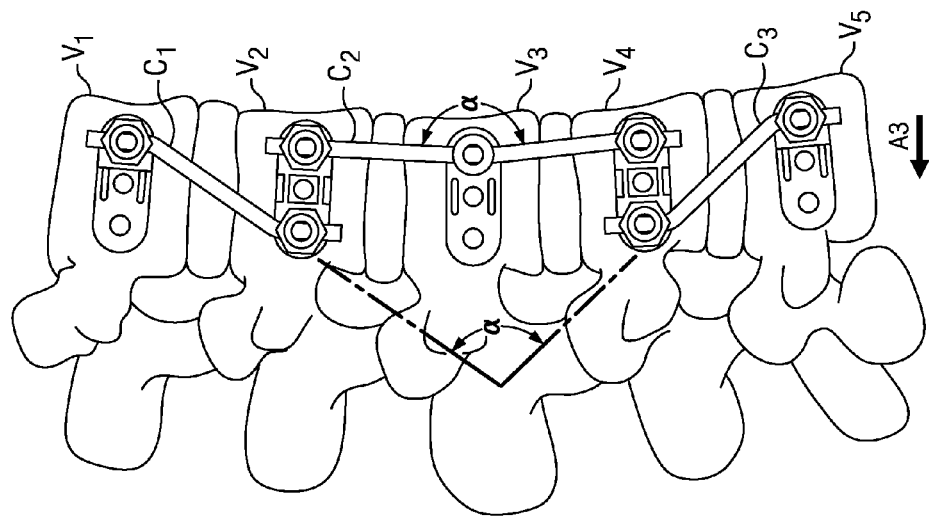
Figure 23H:
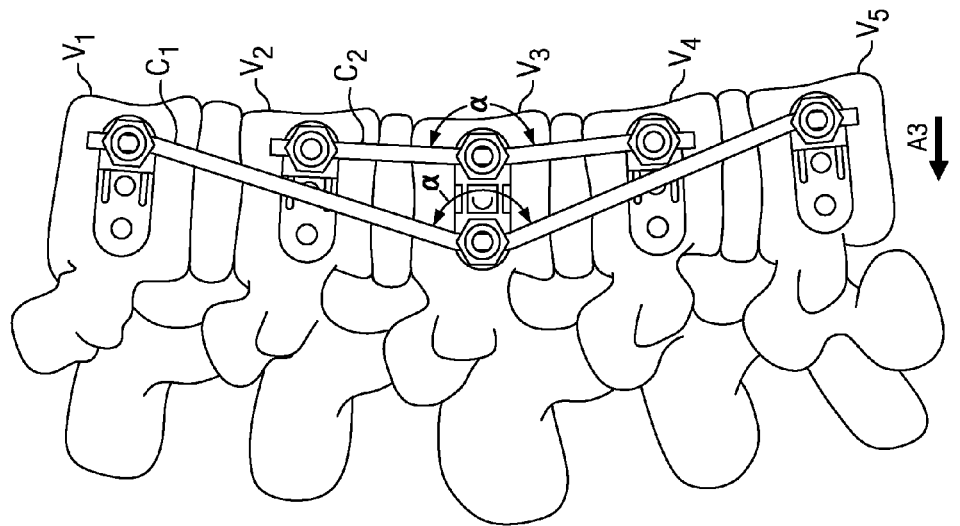
Figure 23G:
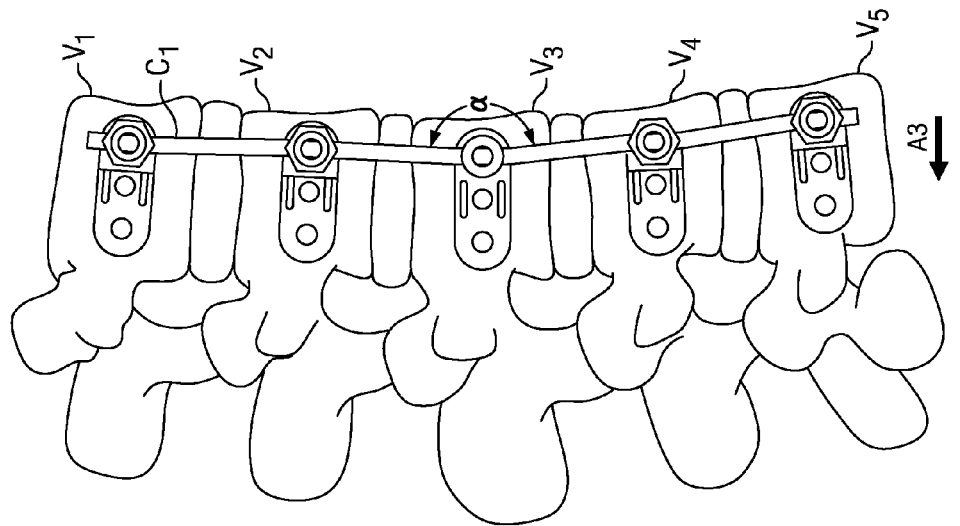

For brevity and ease of discussion, vertebra $V_3$ in each of FIGS. 23(a)-(h) denotes the vertebra at which the apex of the curvature of the spinal deformity is located. Any of the plates disclosed herein can be attached to any of the vertebrae, including vertebra $V_3$, to correct the spinal deformity. In a preferred embodiment, as shown in FIG. 23(a), plate 500 is shown attached to vertebra $V_3$ at the apex of the curvature of the spinal deformity. In that regard, because flexible connection members pass through channel 516 of plate 500 without being rigidly secured to the plate a more even distribution of tension occurs across the entire pate and flexible connection member while still permitting corrective forces across the linked plate members. Thus, it can be advantageous to attach plate 500 to the vertebra at which the apex of the curvature of the spinal deformity is located.

Similarly plates 600 and 700 can be advantageous to attach to the vertebra at which the apex of the curvature of the spinal deformity is located (e.g. $V_3$). In that regard, as discussed above, plate 600 allows for rotation of post 602 about axis L9. The rotation of post 602 about axis L9 allows for a greater degree of freedom in alignment of a flexible member with respect to post 602. Likewise, plate 700 can be advantageous at the apex of the curvature of the spinal deformity because post 702 allows a flexible connection member to be side loaded through side opening 718 into channel 720. The side opening of post 702 allows for an easier capture of a flexible connection member by plate 700. Additionally, because flexible connection members pass through the channels of plates 600 and 700 without being rigidly secured to the respective plates a more even distribution of tension occurs across the entire pate and flexible connection member while still permitting corrective forces across the linked plate members. Thus, it can be advantageous to attach plates 600 and 700 to the vertebra at which the apex of the curvature of the spinal deformity is located.

With reference to FIGS. 23(*a*)-(*h*), plate members 100, 200, 300, and 400 are advantageous to be positioned superior and inferior to the apex of the curvature of the spinal deformity. In that regard, plate members 100, 200, 300, and 400 rigidly secure the flexible connection members $C_1$, $C_2$, and/or $C_3$ to the plate members thereby maintaining or retaining any tension applied to flexible connection members secured to the plate members. In other words, because plate members 100, 200, 300, and 400 rigidly secure the flexible connection members $C_1$, $C_2$, and/or $C_3$ to the respective plate members, any tension applied to flexible connection members is transferred to the plate members as well. As discussed below, the tensioning of the flexible connection members and the respective plate members results in the plate members moving at least one vertebra of the spinal column in order to correct the spinal deformity.

As shown in FIGS. 23(*a*)-(*h*), the plate members and flexible connection members $C_1$, $C_2$, and $C_3$ are positioned superior and inferior to the apex of the curvature of the spinal deformity to create at least one angle α across the apex of the spinal deformity (e.g. V3). In use, flexible connection members $C_1$, $C_2$, and/or $C_3$ are tensioned and the plate members retain and hold the tension placed on the flexible connection members. Tensioning the flexible connection members $C_1$, $C_2$, and $C_3$ in turn causes tension on the plate members that are attached to the respective vertebral bodies. This tension results in the plate members moving the vertebrae in the direction of arrow A3. By moving the vertebral bodies in the direction of arrow A3 the at least one a angle increases to alter or change the curvature of the spinal column in order to correct or modify the spinal alignment thereby addressing the spinal deformity.

It should be noted that the movement of the vertebral bodies in the direction of arrow A3 may occur over time. For example, the movement of the vertebral bodies in the direction of arrow A3 may occur with the growth of the spinal column.

FIGS. 23(*a*)-(*h*) are for exemplary purposes only. Theses figures in no way imply any limitation on the ensemble of plates selected and/or the order of plates disposed along a patient's spinal column. In other words, any of the plates disclosed herein can be attached to any vertebra along a patient's spinal column and used in any order/combination. Furthermore, the specific ensemble of plates can be chosen by a healthcare provider based on the patient's particular spinal deformity.

Although shown in FIGS. 23(*a*)-(*h*) as an ensemble of five plate members secured across five vertebrae, this in no way implies a limitation on the arrangement of the plate members, the configuration of the plate members, the number of plates utilized, and/or the number of vertebrae across which the system disclosed herein can be used. Furthermore, the plates disclosed herein are not limited to attachment to adjacent vertebrae along a patient's spinal column. In that regard, the plates can be spaced apart from one another such that at least one vertebra along an ensemble of plates does not have a plate secured to it.

In some embodiments, the plate channel is not perpendicular to the length of the plate, but instead angles at an oblique angle relative to the length of the plate. For example, with reference to FIG. 23*a*, the channel on the plate may be aligned such that the channel extends in the direction of the dashed lines creating the angle α. In other embodiments, the channels may be angled at 45° relative to the length dimension of the plate. This may accommodate angled take-off for oblique ligament positioning.

The plates disclosed herein are in whole or in part may be constructed of biocompatible materials of various types including metals or polymers. For example, the plate can be constructed of the following biocompatible materials, but are not limited to, cobalt-chromium alloys, titanium alloys, nickel titanium alloys, and/or stainless steel alloys, plastics and polymers including without limitation any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE.

Furthermore, it should be noted that these materials can be coated or treated to render the materials more or less suitable for bone adherence or tissue adherence. Therefore, the plates disclosed herein are in whole or in part may be constructed of biocompatible materials of various types that can be coated or treated to render the plates more or less suitable for bone adherence or tissue adherence.

While the present invention has been illustrated by the above description of embodiments, and while the embodiments have been described in some detail, it is not the intention of the applicant to restrict or in any way limit the scope of the invention to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general or inventive concept. It is understood that all spatial references, such as "longitudinal axis," "horizontal," "vertical," "top," "upper," "lower," "bottom," "left," and "right," are for illustrative purposes only and can be varied within the scope of the disclosure.

What is claimed is:

1. An apparatus for attachment to a vertebral body for treating spinal deformities, the apparatus comprising: a plate member having an upper surface and a lower surface, the upper surface having at least one receiving member defining a channel for receiving a flexible connection member and further comprises a recess radially extending along the upper surface at an angle from the channel to an outer edge of the plate member, the at least one receiving member having a proximal portion and a distal portion, the proximal and distal portions interfacing along a frangible connection such that the at least one receiving member extends axially from the upper surface a first distance when the frangible connection is unbroken and the at least one receiving member extends axially from the upper surface a second distance when the frangible connection is broken, wherein the second distance is less than the first distance.

2. The apparatus of claim 1, wherein the frangible connection comprises a groove extending about the receiving member between the proximal and distal portions.

3. The apparatus of claim 1, wherein the frangible connection comprises at least one aperture extending about the receiving member between the proximal and distal portions.

4. The apparatus of claim 1, wherein the second distance is about 50% to about 70% less than the first distance.

5. The apparatus of claim 1, wherein in the channel axially extends below the upper surface and communicates with the recess, wherein the recess extends from the channel at the angle ranging from about 0 degree to about 30 degree.

6. The apparatus of claim 1, wherein the proximal portion is one integral portion when the frangible connection is broken.

7. The apparatus of claim 1, wherein the at least one receiving member has an exterior surface having external threads that are interrupted and chamfered to define at least one opening into the channel.

8. A system for correcting spinal deformities, the system comprising: a plate having an upper surface and a lower surface, the upper surface having at least one receiving member defining a channel and a groove radially extending along the upper surface at an angle from the channel, the channel extending through the receiving member and defining a first longitudinal axis, the receiving member having a first configuration in which the receiving member extends a first distance from the upper surface and a second configuration in which the receiving member extends a second distance from the upper surface, wherein the first distance is greater than the second distance; a flexible connection member extending through the channel of the plate and extending along the groove at the angle with respect to the channel; and a locking member engaging the receiving member to rigidly secure the flexible connection member within the channel of the plate.

9. The system of claim 8, wherein the at least one receiving member has a bore extending along a second longitudinal axis, the bore configured to receive and guide a fastener to secure the plate to the vertebral body.

10. The system of claim 9, further comprising the fastener positioned within the bore to secure the plate to the vertebral body, wherein a head of said fastener causes a deformation along a portion of the flexible connection member when the locking member engaging the receiving member to rigidly secure the flexible connection member within the channel of the plate, the deformation preventing the fastener from backing out of the bore and increasing the resistance to movement of the flexible connection member along the first longitudinal axis.

11. The system of claim 8, wherein the channel has a key hole shape profile when the at least one receiving member is in the first configuration and a u-shape profile when the at least one receiving member is in the second configuration.

12. The system of claim 8, wherein the channel axially extends below the upper surface and communicates with the groove, the groove extending at the angle ranging from about 0 degree to about 30 degree.

13. The system of claim 8, wherein the at least one receiving member has a proximal portion and a distal portion, the proximal and distal portions interfacing along a frangible connection such that in the first configuration the proximal portion is connected to the distal portion via the frangible connection and in the second configuration the proximal portion has been separated from the distal portion along the frangible connection.

14. An apparatus for attachment to a vertebral body for correcting spinal deformities, the apparatus comprising: a plate having an upper surface and a lower surface, the upper surface having a first end portion and an opposing second end portion, the first end portion having a receiving member defining a channel extending through the receiving member along a first longitudinal axis and defining a bore extending through the receiving member along a second longitudinal axis, the receiving member further comprising a pair of opposing lateral openings providing access to the channel such that the pair of lateral openings are non-aligned with one another and are offset from the first longitudinal axis, the channel being configured for receiving a flexible connection member and the bore being configured to receive and guide a first fastener to secure the plate to the vertebral body, the second end portion having an aperture formed within the upper surface and extending through to the lower surface, the aperture being configured to receive and guide a second fastener to secure the plate to the vertebral body.

15. The apparatus of claim 14, wherein the receiving member is rotatably coupled to the plate such that the receiving member is configured to rotate about its axis.

16. The apparatus of claim 14, wherein the receiving member is a hook.

17. The apparatus of claim 16, where the hook is formed of a pair of base sections with a cantilevered arc section extending between the base projections, the cantilevered arc section having a projection extending along an outer edge.

18. The apparatus of claim 17, wherein the projection extends radially toward the upper surface such that a distal end of the projection remains spaced apart from the upper surface to define a side opening into the channel, the side opening allowing the flexible connection member positioned adjacent the side opening to be hooked under the projection to access the channel.

* * * * *